United States Patent [19]

Powers et al.

[11] Patent Number: 4,702,732
[45] Date of Patent: Oct. 27, 1987

[54] ELECTRODES, ELECTRODE ASSEMBLIES, METHODS, AND SYSTEMS FOR TISSUE STIMULATION AND TRANSDERMAL DELIVERY OF PHARMACOLOGICALLY ACTIVE LIGANDS

[75] Inventors: Whitney R. Powers, Topsfield, Mass.; Henry Sisun, Pawtucket, R.I.

[73] Assignee: Trustees of Boston University, Boston, Mass.

[21] Appl. No.: 935,057

[22] Filed: Nov. 21, 1986

Related U.S. Application Data

[63] Continuation-in-part of Ser. No. 685,425, Dec. 24, 1984, abandoned.

[51] Int. Cl.$^4$ .............................................. A61N 1/30
[52] U.S. Cl. ...................................... 604/20; 128/639; 128/798; 128/803; 29/592 R
[58] Field of Search .................. 604/20; 128/639, 640, 128/642–644, 798, 803; 29/592 R

[56] References Cited

U.S. PATENT DOCUMENTS

| | | | |
|---|---|---|---|
| 3,520,297 | 7/1970 | Bechtold | 604/20 |
| 3,610,229 | 10/1971 | Zenkich | 128/641 |
| 3,618,601 | 11/1971 | Richardson | 604/20 |
| 3,746,004 | 7/1973 | Jankelson | 128/803 |
| 3,901,218 | 8/1975 | Buchalter | 128/641 |
| 3,976,055 | 8/1976 | Monter et al. | 128/641 |
| 4,090,752 | 5/1978 | Long | 128/641 |
| 4,109,648 | 8/1978 | Larke et al. | 128/639 |
| 4,126,126 | 11/1978 | Bare et al. | 128/639 |
| 4,141,359 | 2/1979 | Jacobsen et al. | 604/20 |
| 4,211,222 | 7/1980 | Tapper | 604/20 |
| 4,237,886 | 12/1980 | Sakurada et al. | 128/798 |
| 4,273,135 | 6/1981 | Larimore et al. | 128/640 |
| 4,383,529 | 5/1983 | Webster | 604/20 |
| 4,406,658 | 9/1983 | Lattin et al. | 604/20 |
| 4,406,827 | 9/1983 | Carim | 128/639 |
| 4,416,274 | 11/1983 | Jacobsen et al. | 604/20 |
| 4,474,570 | 10/1984 | Ariura et al. | 604/20 |
| 4,515,162 | 5/1985 | Yamamoto et al. | 128/640 |

FOREIGN PATENT DOCUMENTS

| | | | |
|---|---|---|---|
| 0663412 | 5/1979 | U.S.S.R. | 604/20 |
| 0856462 | 8/1981 | U.S.S.R. | 604/20 |
| 1012923 | 4/1983 | U.S.S.R. | 604/20 |

OTHER PUBLICATIONS

"Iontophoresis: The Non-Invasive Administration of Drugs", Motion Control brochere of Phoresor, 1979.

Primary Examiner—Kyle L. Howell
Assistant Examiner—Ruth S. Smith
Attorney, Agent, or Firm—Prashker, David

[57] ABSTRACT

A novel electrode and electrode assembly is provided which preferably uses alternating and direct electrical energy for transdermal delivery of pharmacologically active ligands and for stimulation of tissues in-vivo. Methods and systems are also disclosed which allow a broad range of therapeutic agents to be transmitted to tissues and organs superficially or deep within the body.

27 Claims, 11 Drawing Figures

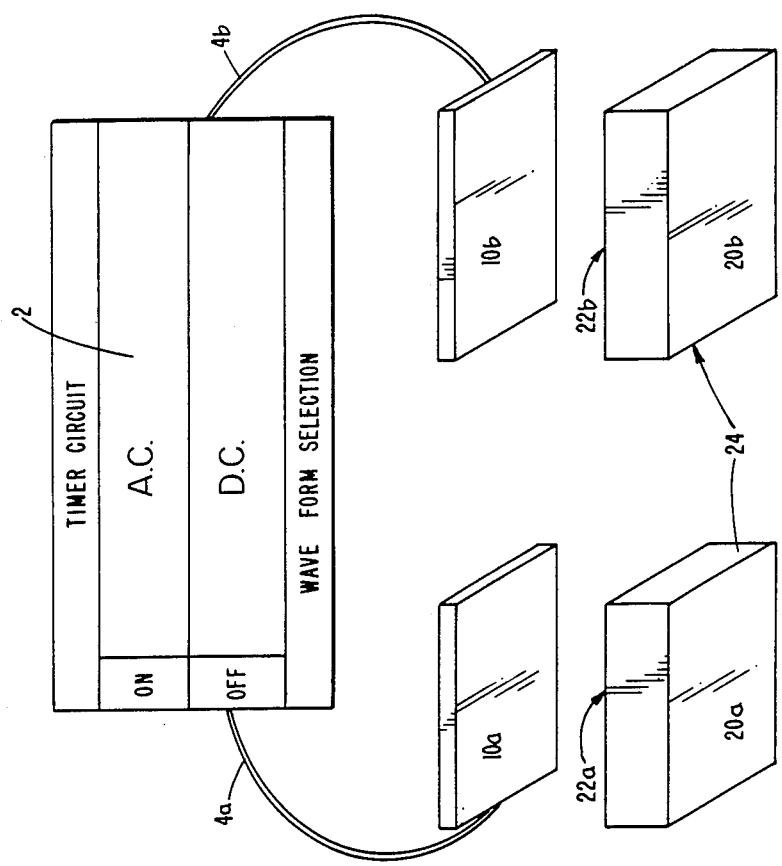

FIG 4
RELAXATION PERIOD
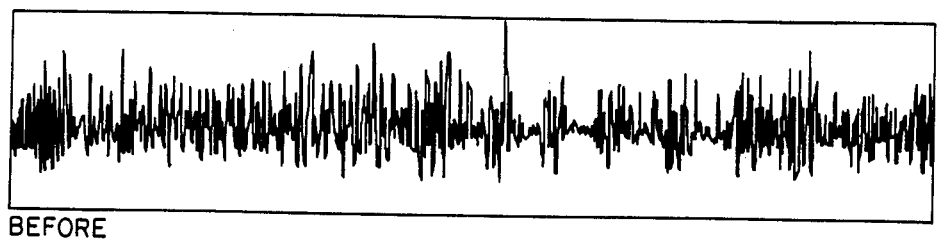
BEFORE
AFTER
ACTIVE MUSCLE CONTRACTION
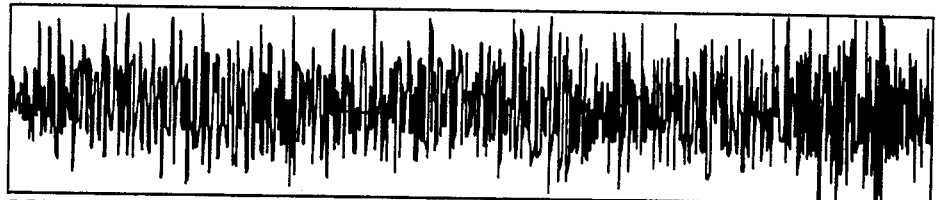
BEFORE
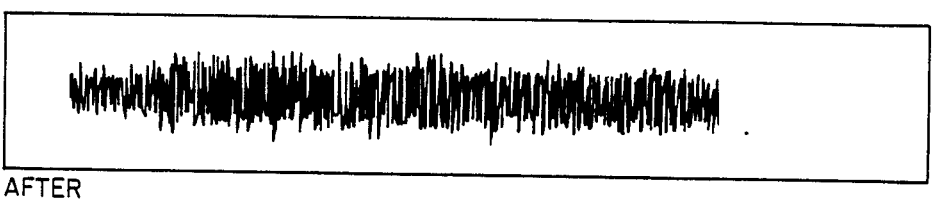
AFTER
RELAXATION AFTER MUSCLE CONTRACTION
BEFORE
AFTER

ELECTRODES, ELECTRODE ASSEMBLIES, METHODS, AND SYSTEMS FOR TISSUE STIMULATION AND TRANSDERMAL DELIVERY OF PHARMACOLOGICALLY ACTIVE LIGANDS

CROSS-REFERENCE

This application is a continuation-in-part of application Ser. No. 685,425 filed Dec. 24, 1984, now abandoned.

FIELD OF THE INVENTION

The invention is generally concerned with apparatus and methods which utilize energy for therapeutic purposes and is specifically concerned with electrodes which actively deliver therapeutic agents transdermally on demand.

BACKGROUND AND DESCRIPTION OF THE PRIOR ART

The therapeutic uses of energy for curative and preventative effects upon the human body have been known for many years. Of the various available types, electrical energy given in adequate strength and duration is the most common. The two principal effects of electrical energy upon tissues in vivo are the ionic (or chemical) effect which draws charged ions and particles towards an oppositely charged pole; and the heating (or thermal) effect which produces physiologically active amounts of heat. These principal changes in turn affect cellular activity and produce a variety of secondary physiological changes such as activity changes in the sensory vasomotor system; actions on the neuromuscular system, pH, intramembrane and salt concentration modifications; and changes in local and general metabolism. The variety of apparatus and techniques utilizing these changes now encompasses medical diathermy, hyperthermy, electrosurgery, electrical stimulation of nerves and muscles, and the use of iontophoresis for delivery of therapeutic agents. [Richard K. Kovacs, *Electrotherapy and Light Therapy*, Lea and Febiger, 1949; William J. Shriber, *A Manual of Electrotherapy*, 4th Ed., Lea and Febiger, 1978]. Of these, the therapeutic value of iontophoresis and electrical stimulation of tissues in vivo has increased enormously in recent years.

Transcutaneous electrical nerve stimulation (hereinafter "TENS") is beneficial for analgesic purposes to symptomatically relieve acute and/or chronic pain. Although the mechanism by which analgesia occurs in response to external nerve stimulation is not yet fully understood, it is well established that such analgesia does occur safely and effectively [Sjolund et al., *Advanced in Pain Research and Therapy* 3:587–592 (1979); Serrato, J. C., *Southern Medical Journal* 72:67–69 (1979)]. In TENS therapy, the afferent structures of the peripheral nervous system are the targeted sites for low voltage sinusoidal (alternating) current stimulations. Since pain is a sensory phenomenon within these afferent structures, the process of passing alternating electrical current across the skin directly influences the peripheral nervous system responses and creates an analgesic effect [Mannheimer, J. S. and Laupe, G. N., *Clinical Transcutaneous Electrical Nerve Stimulation*, Chapter 6, F. A. Davis Co., 1984].

Initially, electrode systems for TENS used sponges and bulk metallic wires and probes which were connected to large stationary sources of A.C. power. Such systems were of limited usefulness. In recent years, a number of commercially manufactured portable electrodes have become available to the public for TENS applications. These electrodes contain pads composed of natural or synthetic gums and gels as the materials directly in contact with the skin of the subject exemplified by the Tenzcare electrode series (3M Co.), NEURO-STIM electrodes (Consolidated Medical Equipment Inc.), Lectec karaya gum electrodes (Lectec Corp.), SUE karaya gum electrodes (Empi, Inc.), Staoderm karaya gum electrodes (Staodynamics, Inc.), and UNI-PAD natural gum electrodes (Uni-Patch, Inc.). Taken together, they form a single class of TENS electrodes with commonly shared characteristics: a construction and utility so as to be one-time use units; poor adhesion to the skin and poor cohesion qualities in the gum pads; and, a recurring tendency to irritate the skin of the user. These deficiencies have substantially reduced the effectiveness and therapeutic value of TENS electrodes.

Another, completely different, application of electrical energy is low-voltage neuromuscular stimulation to restore or improve the function of *efferent* motor nerve units. In these neuromuscular applications, alternating current (AC) sources are used to directly stimulate the efferent motor nerve structures in the muscle tissue and are often supplemented by direct current (DC) stimulation of denervated muscles. Neuromuscular stimulation is most beneficial in those instances in which natural muscle function is lost or diminished due to trauma; the use of electrical current offers restoration of function using artificial stimulation, directly encourages volitional effort on the part of the patient to maintain the muscle's contractility and nutritional requirements, and acts as partial blockers of noxious inputs. Although the earliest experimental work was performed by Reid in 1841 at the University of Edinborough, much controversy regarding the therapeutic effectiveness of electrical muscle stimulation followed which was resolved only about forty years ago [Fischer, *An Jour. Physiol.* 127:605 (1939); Gutman et al., *Lancet* 1:169 (1942); Liebesny, *Arch. Phys. Ther.* 23: (1942); Hines et al, *Arch. Phys. Ther.* 24:69 (1943)]. Today, the recognized therapeutic values include: restoration of tone to injured muscles; prevention of intermuscular and intramuscular adhesions; the ability to keep the tendons and other parts moving so they do not become adherent to contiguous structures; and, above all, the ability to increase the blood supply to the injured tissues thereby accelerating the rate of repair by rapidly promoting absorption of waste products.

Originally, electrode apparatus for muscle stimulation consisted of only a steel or other metallic probe which was directly connected by bulk wires to a source of electrical energy. Presently available electrodes are an improvement only in that a pad formed of natural or synthetic polymers now serves as the contact surface for the skin; the various electrical circuits are attached to the polymer pad and the electrical energy is now transmitted first to the pad rather than directly to the muscular tissue. Such electrodes are exampled by the CONDUCTOL foam and karaya gum electrodes of Zimmer, Inc.

Iontophoresis, on the other hand, is a technique for the therapeutic introduction of one or more ions in solution into the tissues of the body by means of a galvanic or direct electrical current. The technique is an active delivery system for the transportation of ionized pharmacologically active ligands such as drugs through intact skin based on using the principle that ions in solution will migrate in the presence of a charged electrical field. In its most common form, iontophoresis is performed by placing a transmitting electrode containing a reservoir of material saturated with an ionized drug onto the skin of the subject at the site where the drug is to be introduced. A second electrode without any ionized drug is positioned on the skin usually in opposition to the first electrode. A direct current is applied to each electrode which then becomes either positive or negatively charged in accordance with the charge of the current given. The ionized drug in the reservoir material, having been chosen to be of the same polarity as the charged first electrode itself, is driven out of the reservoir material towards the oppositely charged second electrode which acts to attract the ionized drug towards it. In this manner, the ionized drug passes out of the reservoir material and thus migrates transcutaneously through the intact skin at the desired location in its effort to each the oppositely positioned second electrode. Insofar as is presently known, only galvanic or direct electrical current has been effective for iontophoresis.

Iontophoresis, therefore, is an active method or system for transdermal delivery of pharmacologically active drugs or ligands in general. Active delivery systems are very different and distinguishable from passive drug delivery systems. Passive systems rely on natural forces and pressures such as diffusion, solubility and/or concentration density gradients for transportation and delivery of the drug or ligand into the tissues of the body; characteristically, passive systems require direct intimate contact of the drug or ligand with the skin of the subject for days or even weeks at a time and rely upon a slow, continuous, delivery of the drug in limited concentration to achieve the therapeutic effect. A detailed description of the variety of uses and inherent limitations of passive drug delivery systems and an evaluation of polymeric formulations for passive devices is provided in *Water-Soluble Polymers*, N. M. Bikales Editor, Plenum Press, 1973 and in *Controlled Release Polymeric Formulations*, D. R. Paul and F. W. Harris Editors, American Chemical Society, 1976.

Iontophoresis, on the other hand, is an actively driven system which relies on the ionization of the drug or other pharmacologically active ligand in a liquid or paste into positively and negatively charged ions and then utilizes direct (galvanic) current to propel the charged ions through the skin using a pair of oppositely charged electrodes. This phenomenon—the introduction of drugs in solution into the body—is directly due to the action of the direct current and is not caused by simple absorption of the skin from the wet pad soaked with the drug. This first was proven by the now classical animal experiments of Leduc who was the chief originator of the iontophoretic mode of medication [Leduc, S., *Electric Ions And Their Use In Medicine*, London Rebman Ltd., 1908] and confirmed subsequently by Puttermans et al. *Arch. Phys. Med. Rehabil.* 63:176-180 (1982) and the references cited therein.

Unfortunately, subsequent research and development of iontophoretic apparatus has focused predominantly on the parameters of using galvanic current with relatively little attention, if any, to the effects and deficiencies of the material serving as the reservoir holding the ionized drug in the electrode and/or the condition of the skin or targeted tissue in the person receiving the medication [Kovacs, R., *Electro Therapy And Light Therapy*, 6th ed., Lea and Febiger, Philadelphia, 1949, pp. 153-165]. As a result, a series of axiomatic principle or iontophoresis have evolved and been so generally accepted as being now virtually incontestible. These axioms are: (1) Ions move at a fixed rate of speed which increases with the voltage applied to the electrode; as a corrollary, the current intensity (in millamperes) used in iontophoresis should generally be the maximum current that can be tolerated by the patient with a minimal of discomfort. (2) Ions, without regard to molecular weight, cannot and do not migrate far below the surface of the skin (epidermis and dermis) and consequently medication via iontophoresis is essentially a local or intradermal form of treatment; systemic effects, if any, are an exception and are not to be expected. (3) The time necessary for ionized drug transfer will vary with the characteristics and the potency of the specific drug; a therapeutic treatment period, regardless of electrode construction will vary nominally from five minutes to several hours or even days in duration. (4) The reservoir material in the electrode containing the ionized drug in solution should be an absorbent material of substantial thickness or take the form of a medicated water bath; the concentration of all drugs in solutions retained and held by the reservoir material within the electrode should be one percent or less as no advantage is gained by increasing the concentration of the drug in solution above this 1% level. [Kovacs, R., *Electrotherapy And Light Therapy*, 6th ed., Lea and Febiger, Philadelphia, 1949; Kahn, J., *Low Voltage Technique*, 3rd ed., New York, 1978; Shriber, W. J., A Manual Of Electrotherapy, 4th ed., Lea and Febiger, Philadelphia, 1978].

Because of these dogmatic axioms, nearly all of the recent advances in this art have been directed to one of two areas: specific therapeutic applications for iontophoresis whereby systemic toxicity can be virtually eliminated by using minute amounts of drug in high concentration delivered at a localized site; and specific improvements in the electrical circuitry of the energy source or electrode assembly as exemplified by the improved electrical controls and safety circuits which enhance the safety and comfort aspects for the subject. Each of these areas represent divergent directions of research which, although individually useful, accept and rely upon the general axioms previously stated. Exemplifying the development of specific therapeutic applications for iontophoresis are the following: administering pilocarpine in a diagnostic test for cystic fibrosis in infants and children [Gangarosa, L. P., *Meth, And Find. Exp. Clin. Pharmacol.*, 2:105-109 (1979); local anaesthesia of the eardrum [Comeau et al., *Arch. Otolaryngyl.* 98:114 (1973)]; iontophoretic delivery of idoxuridine for recurrent herpes labialis [Gangarosa et al., *Meth. And Find. Exptl. Clin. Pharmacol.* 1:105-109 (1979)]; anaesthesia of the tympanic membrane [Brummett et al., *Trans. Am. Acad. Aphthalmol. Otolaryngol.* 78:453 (1974)]; delivery of dexamethasone for reduction of inflammation [Glass et al., *Int. Soc. Trop. Dermat.*, 19:519-524 (1980)]; anaesthesia for tooth extraction [Gangaroas et al., *Meth. Find. Exp. Clin. Pharm.* 3:83-94 (1981)]; and delivery of heavy metals (e.g., copper and zinc) and of vasodilating drugs (histamine, mechoylyl, cocaine, epinephrine, and aconitine) [Shriber, W. J., *A Manual Of Electrotherapy*, 4th ed., Lea and Febiger, Philadelphia, 1978].

In direct contrast, efforts to improve the electrical circuitry of the power source or the electrode assembly are illustrated by the following: use of a light-coupled pulse generator and current monitor [Waud, D. R., *J. Appl. Physiol.* 23:128-130 (1967)]; a completely self-contained electrode [U.S. Pat. No. 3,677,268]; an iontophoretic device with reversible polarity [U.S. Pat. No. 4,406,658]; an electrophoretic device whose current is periodically interrupted by relatively short pulse of current in the opposite direction [U.S. Pat. No. 4,340,047]; a self-contained iontophoretic apparatus with a pair of electrodes in close proximity to one another [U.S. Pat. No. 4,325,367]; a method of applying electricity to a selected area to minimize burning of the skin [U.S. Pat. No. 4,211,222]; a burn protection electrode structure [U.S. Pat. No. 4,164,226]; specific circuitry for application of fluoride in teeth [U.S. Pat. No. 4,149,533]; and a current adjustment circuit for iontophoretic electrodes [U.S. Pat. No. 3,991,755].

It is apparent that there has been very little interest in or attention to that singular component of the iontophoretic electrode which retains and holds the active ionized drug to be delivered—the material forming the reservoir. For many years, the now classical method for iontophoresis required only a reservoir material which was absorbent and of sufficient thickness to accept a stainless steel probe. Materials considered suitable for use as a reservoir included paper (often in the form of paper towels); household towels made of cotton, cellucotton or felt; and even asbestos fabric. Traditionally, the chosen reservoir material was soaked in warm water, covered with a block of tin foil cut to meet the dimensions of the reservoir and held in position using a sandbag or rubber bandage.

This melange, comprising the electrode proper, was then placed over the target area. The skin in this area was previously massaged with the ionized ligand in ointment form, or washed with a towel previously soaked in the medicated solution if it was dispersed in a fluid. Galvanic current was conveyed to the reservoir material using alligator chips attached to the tin foil backing and/or by lead wires attached to the current source. [Shriber, W. J., *A Manual of Electrotherapy*, 4th ed., Lea and Febiger, Philadelphia, 1978; Kovacs, R., *Electrotherapy And Light Therapy*, 6th ed., Lea and Febiger, Philadelphia, 1949, p. 156].

Only recently has there been any departure from the classical approach with regard to the materials which may be suitable for use as the reservoir in an iontophoretic electrode. For example, Jacobsen et al., demonstrated that some gels comprising as karaya gum and other polysaccharides are nominally useful as reservoir materials if the thickness-to-width ratio is restricted to about 1:10 [U.S. Pat. No. 4,416,274]. A secondary development by Jacobsen et al., was an electrode having a discrete chamber or enclosure for the dispersion of a drug within a liquid carrier prior to driving the ions through a microporous membrane for migration into the subject [U.S. Pat. No. 4,419,092]; this particular device has been commercialized by Motion Control, Inc. and commercial embodiments are now available to the public. The use of agar-agar gels in a cup-like receptacle for ionized drug delivery has also been described [U.S. Pat. No. 4,383,529]; unfortunately, agar-agar has been found to degrade upon addition of galvanic current and thus delivers degradation byproducts such as proteins and iodine to the targeted site concomitantly with delivery of the drug. Often these byproducts are unwanted or are undesirable in the subject.

Overall therefore, while advances have occurred enlarging the therapeutic uses of energy, it is apparent that there has been little consistency in approach, no analysis of common problems, and no overlap of structural design efforts for improving electrode apparatus and assemblies. To the contrary, each type of electrode (be it for transcutaneous nerve stimulation, or for neuromuscular stimulation, or for iontophoresis) has been altered and designed independently with almost a complete disregard of the advanced in other types of electrodes. Although there now appear to be some commonly shared features among them (particularly in commercially available embodiments), there has been no recognition and no awareness to date that the choice and characteristics of the material to be used as the pad or reservoir is the major, if not decisive, factor in determining the compatibility and effectiveness of electrodes generally without regard to application.

SUMMARY OF THE INVENTION

An electrode and electrode assembly is provided which is suitable for a wide variety of therapeutic applications comprising: a source of energy which includes electricity, laser light, ultrasound, microwave, and magnetism; a hydrophilic, porous polymeric matrix which supports a confluent aqueous phase and has an initial resistance not greater than 500 ohms per square inch in the absence of an electrically conductive salt solution above 1.0% in concentration; and means for conveying the energy from its source to the polymeric matrix. The invention also comprises methods and active delivery systems utilizing the electrode for transdermal delivery of pharmacologically active ligands on demand to a localized site; and for transcutaneous nerve stimulation and neuromuscular stimulation which may be administered in combination with ligand delivery. The electrode, electrode assembly and methods do not rely upon a single class of chemical compositions to be effective; are able to deliver a broad range of therapeutic agents to tissues and organs superficially or deep within the body; and may be employed in a variety of alternative modes at specified time intervals without discomfort to the subject.

DETAILED DESCRIPTION OF THE DRAWING

The present invention may be more fully and clearly understood when taken in conjunction with the accompanying drawing, in which:

FIG. 1 is a preferred embodiment of the electrode assembly which utilizes electrical energy.

FIGS. 4a-4c, represent recordings of electromyography impulses in alternative modes before and after delivery of lidocaine.

DETAILED DESCRIPTION OF THE INVENTION AND OF THE PREFERRED EMBODIMENTS

Figure 2A:
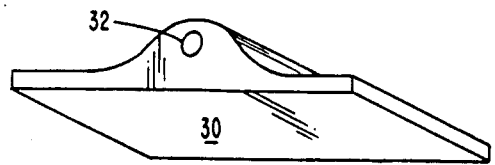
FIGS. 2a-2d' are alternate embodiments of commercially available conductive members useful with the electrode assembly illustrated in FIG. 1.

The present invention as a whole comprises an electrode, an electrode assembly and methods and delivery systems for using these articles in therapeutic applications with human and animal subjects. The electrode described herein is particularly useful for transdermal delivery of pharmacologically active ligands such as drugs to a localized site on demand. One of the primary advantages in using these articles, assemblies and methods is the ability to deliver the desired ligand in concentrated dosages to a specific tissue site or organ located either superficially or deep within the body without incurring systemic toxicity. It has been long recognized that many drugs, in spite of their therapeutic effects, are nevertheless dangerous or hazardous agents because of their systemic side effects. Each drug has a recognized range of therapeutic and toxic dosages which varies with the method of administration. Optimally, a drug should not be delivered before it is actually needed; however, when it is needed, the drug should be given rapidly, to only the specific site, and in sufficient dosage to be effective. Moreover, the mode and speed of drug delivery should be controllable so that drug delivery may be ended if and when necessary; similarly, slower rates of drug delivery over longer time intervals should also be available if and when required. The present invention fulfills each of these needs and provides the long sought-after degree of control.

The electrode, electrode assemblies, and methods are also useful for transcutaneous electrical nerve stimulation (TENS) and neuromuscular stimulation therapy when sinusoidal (alternating) electrical current and/or galvanic (DC) electrical circuitry are used. Superficially located afferent nerve endings and efferent motor nerve structures may be electrically stimulated using this apparatus and these respective therapies may be combined within the same electrode to also deliver ligands on demand. The combination therefore of muscular or nerve stimulation which is followed or preceded by, or occurs simultaneously with, delivery of a pharmacologically active ligand using the same equipment thus provides features and advantages previously unknown in this art.

The preferred embodiment of the electrode and the electrode assembly is illustrated in FIG. 1 where the A.C. and the D.C. energy sources are integrated printed circuits in a single portable battery powered unit. The circuitry includes such recognized features as programmable microprocessor silicon chips and compatible software, variable voltage and amperage regulators, safety circuits, automatic cut-off circuits, time dependent on-off switches, and automatic timing devices. The specific circuitry employed to form the apparatus illustrated in FIG. 1 is presently available in many sizes and shapes from a variety of commercial manufacturers and is thus represented in block diagram form.

As seen in FIG. 1, the preferred embodiment is an electrode assembly comprising a combined source of alternating and direct current 2 which is in electrical communication with conductive members 10a and 10b via electrical wire leads 4a and 4b. The electrical energy source 2 may be formed in any desired circuitry and exist in bulk component form or in a printed circuit format. The conductive members 10a and 10b are disposed upon polymeric matrices 20a and 20b whose composition and characteristics will be described hereinafter. By definition, the lead 4a and conductive member 10a together with the polymeric matrix 20a comprise a first electrode "A" while electrical lead 4b and conductive member 10b in combination with polymeric matrix 20b comprise a second electrode "B". When these electrodes A and B are individually placed in communication with an energy source 2, each becomes an "active" or complete electrode. Active electrode A and active electrode B in combination define an electrode assembly.

When alternating (sinusoidal) electrical current is used, as in transcutaneous electrical nerve stimulation, either active electrode A or active electrode B can serve as the transmitting electrode; however, when direct current is used as for transdermal delivery of a ligand, the transmitting or driving electrode will be the one holding the drug in its polymeric matrix. For descriptive purposes only, electrode A will be presumed to contain an ionized ligand within the matrix 20a, and thus serve as the transmitting electrode. The electrodes A and B are positioned on opposing sides of the limb or target zone as oppositely positioned charged poles if the drug is to be delivered into deep tissues; alternatively, for superficial delivery of drug such as in local anaesthesia, the electrodes A and B are placed several inches apart from each other at the skin site where the ligand is to be introduced. The ionized ligand in the matrix 20a will be repelled by the polarity of active electrode A which has an identical electrical charge and be attracted towards active electrode B which has the opposite electrical charge, all in accordance with the accepted theory of direct current iontophoresis.

Although the therapeutic applications for this invention are presently directed to transdermal drug delivery and to stimulation of tissues in vivo, it will be recognized that other therapeutic uses which are only now being clinically identified, assessed or developed will be able to make use of the present electrode, electrode assembly and methodology. This is particularly accurate and appropriate since the requisite energy source is not limited to only electrical energy but also includes the use of other energies such as laser light energy, ultrasound, microwave, and magnetism. The clinical/diagnostic applications for these alternative energy sources as well as designs for their miniaturization and portability are now being extensively explored and evaluated. In view of the diversity of the present invention as a whole and with a view to the multiple areas of research now in progress, the detailed description will be presented in three distinct parts. The goals of the presentation format are to facilitate recognition of the true scope of the present invention; to properly identify the critical components in the electrode apparatus comprising the invention; to describe the variability of the critical components; and to delineate the methods of using the electrode which are of practical therapeutic benefit.

I. CRITICAL COMPONENTS COMPRISING THE INVENTION

Three essential components comprise the active electrode: a source of energy, a polymer matrix having a minimum of specified characteristics, and means for conveying the energy from its source to the polymer matrix. Each component is described in detail including its preferred embodiment(s) and the degree of variation which is acceptable. The preferred embodiments are those which employ electrical current (either A.C. or D.C. in any form) in conjunction with specified polymeric matrix compositions as the reservoir or pad. While portable embodiments are the preferred forms of the invention, it will be understood that large stationary units comprising the electrode and electrode assembly are equally suitable; and that factors such as size, portability, and degree of miniaturization play no role in defining the critical elements of the apparatus. In this regard, it will be apparent that while many nonelectrical energy sources now exist only in immobile, inconvenient or commercially impractical form, future developments will undoubtedly permit them to be manufactured in miniaturized, portable, and more efficient formats.

Sources of Energy

A variety of energy sources may be used as the active force for the electrode and in electrode assemblies. The immediately available and preferred sources comprise electrical energy in all its forms and include galvanic or direct current, interrupted and surging galvanic current, interrupted sinusoidal or modulated alternating current, and sinusoidal or alternating current. Under public consumer use conditions, these may be grouped into two classes as either direct current (D.C.) or alternating current (A.C.), each of which provides different therapeutic applications. Direct current provides for transdermal delivery of pharmacologically active ligands in ionized form using the mechanism of identity of charge to drive the ionized ligand across the skin and for some neuromuscular stimulation. In comparison, the use of alternating current provides for transcutaneous electrical nerve stimulation for analgesic purposes and for stimulation of muscle tissue via its nerve supply using the same electrode. This is possible because although a ligand is present within the polymeric matrix material (the reservoir) this type of electrical current does not act to repel the charged ions. It is the particular therapeutic application, therefore, that dictates the choice of what type of electrical current is to be used as the energy.

The use parameters for A.C. and/or D.C. applications are the following: The current intensity may vary from 0.1 milliamperes (hereinafter "ma") to 10.0 ma, with a preferred range from 3.5-5.2 ma. The lower range, ~0.1 ma, is useful for very sensitive tissues such as vaginal tissue and the oral mucosa; the 1.0-2.5 ma level is suitable for the face and less sensitive tissues; and the extreme upper values, ~10.0 ma, are for penetrating deeper muscular areas of the lower back or shoulder. The effectiveness of the active electrode and electrode assemblies are best maintained as a function of current intensity (amperage) and not as a function of the voltage. Accordingly, to maintain a constant current intensity, such as 5.2 ma, it will often be necessary to steadily increase the voltage over time because the electrical resistance of the conductive members and matrix will also steadily increase. Generally, the useful voltages vary from 10-90 volts, but preferably are kept in the range of 5-40 volts with direct current to minimize the subject's discomfort.

Time is the most inconstant of the use parameters and will vary with the application and the cumulative effect of the current intensity and the voltage in combination. If tissue stimulation is the application, then any period within the general range of 5-60 minutes duration is acceptable. Sixty minutes is considered the maximum allowable limit with respect to the subject's discomfort in the absence of a reversing polarity circuit which halts and reverses the polarizing ion effect on living tissues caused by electrical current. A 5-15 minute application is a suitable time for facial tissues whereas 20-30 minutes is more appropriate for deep nerves and muscles in the back. Longer treatments times up to 60 minutes, although beneficial, directly increase the degree of risk for polarizing the ions within the subject's tissues. For this reason, the preferred time for delivery of ligands across the skin is 15-30 minutes. Note however that a higher current intensity given over a shorter time will provide a result equal or equivalent to a smaller current intensity given over a longer period of time. For example, 5.0 ma for 5 minutes often provides effects similar to 1-2 ma for 15 minutes. For this reason, time is held to be the least important parameter, particularly in transdermal delivery of ligand applications.

Alternative kinds of energy useful in a variety of therapeutic applications include laser light energy, microwaves, ultrasound, and magnetism. If these other kinds of energy are used for transdermal delivery of a pharmacologically active ligand, it must be recognized that the mechanism whereby the energy (in wave, particle or other form) causes the ligand to migrate out of the polymeric matrix and into the subject will vary with the specific kind of energy used. For example, the waveforms of ultrasound are preferably used in power ranges of 10-20 watts and at frequencies in the range of 10,000-20,000 hertz; based upon presently available knowledge, these waveform types of energy are believed to deliver ligands across the skin as neutral molecules and not as charged ions [Griffith and Karselis, *Physical Agents For Physical Therapists*, 1982; U.S. Pat. No. 4,127,125]. In comparison, an oscillating magnetic field demonstrates its own unique mechanism for delivery of ligands [Siegal et al., "Controlled Release of Polypeptides And Other Macromolecules" in *Pharmaceutical Research*, pp 2-10, 1984; U.S. Pat. No. 4,425,117]. Equally important, different precautions must be taken for each respective kind of energy. For example, if laser energy is applied, the wavelength of the light should be in the lower or "cold" range as higher wavelengths tend to heat and/or liquify the reservoir material thereby rendering the electrode useless; alternatively high frequency or "hot" wavelengths can be utilized in short pulses with minimal effects. Because of the different mechanisms and precautionary measures inherent in each of these alternative energy sources, the selection of an energy type will be determined—first, by the particulars of the therapeutic application; and second, by the availability and conveniene of the energy to the user. It is again emphasized that neither the physical state, dimensions, circuitry, or other requirement for using a specific kind of energy are decisive factors. To the contrary, it is essential only that the energy source interact with the material reservoir in a reproducible manner to achieve the desired therapeutic effect regardless of the particulars of generating the forces in play. No other restrictions or limitations as to energy are meaningful.

Means For Conveying The Energy From Its Source To The Polymeric Matrix

In the embodiment illustrated by FIG. 1 utilizing alternating and/or direct electrical current as the energy source, the electrical leads 4a and 4b and the conductive members 10a and 10b together comprise the specific means for conveying the electrical energy to the polymeric matrices. The electrical leads 4a and 4b may also take the form of bulk wires, printed circuits, or any other form of electrical communication conventionally known in the art. The preferred conductive members however, are thin highly conductive materials such as metals or carbon containing compounds and the like which are configured to conform to the dimensions of the upper surface of each polymeric matrix 20a and 20b. As illustrated in FIG. 1, conductive member 10a is configured in accordance with and has a surface area only slightly smaller than the external surface 22a of the polymer matrix 20a; similarly, the conductive member 10b has a surface area only slightly less than and is configured to match the exterior surface 22b of the polymer matrix 20b. This is desirable because of the effects of direct current on the contents of the polymeric matrix which acts as a charged force to drive identically charged ions essentially unidirectionally through the thickness of the matrix from the point of contact between the conductive member 10a and the polymeric matrix 20b. There are minimal (if any) lateral or radial driving effects created by direct current in the apparatus. Because the forces must be directed through the thickness of the polymeric matrix 20a and 20b if they are to have any practical effect, it is preferred that the perimeter of reservoir matrix 20a be surrounded and covered with a thin film 24 of non-porous electrically resistant material. This will prevent the ionized ligand from being transported in a lateral or radial direction.

Figure 2B:
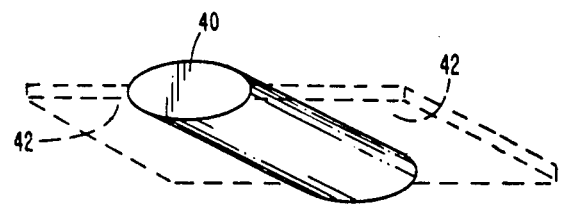
Figure 2C:
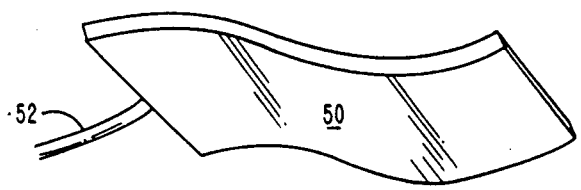
Figure 2D:
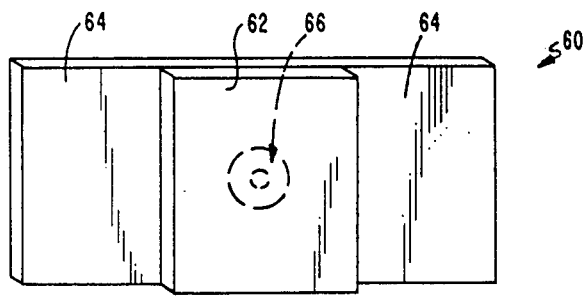
Figure 2D:
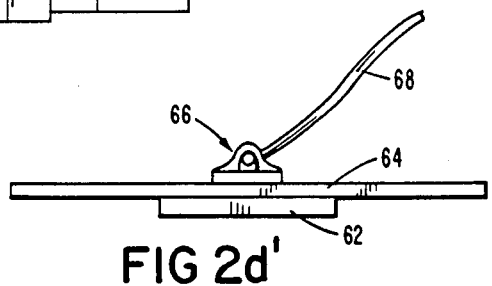

A variety of different conductive members for conveying electrical energy are known, many of which are commercially available from sundry manufacturers. The variety is illustrated in FIGS. 2a–2d respectively, each of which is a conductive member now used in commercially available electrodes for electrical nerve stimulation. FIG. 2a illustrates a rectangular slab 30 formed of carbon or carbon and graphite in combination and a junction 32 for connection of an electrical lead wire (not shown). This member 30 is presently available from UNI-PATCH Inc, (Wabasha, MN). FIG. 2b shows a semicylindrical solid carbon bar 40 which is embedded into the material comprising the pad for contact with the skin pad material 42 overhangs each side of the conductive member as an extended sheet. This conductive member 40 is commercially sold by 3M Co. (St. Paul, MN). FIG. 2c displays a thin, rectangularly shaped metallic foil 50 having a wire lead 52 connected to the source of energy; the foil 50 is directly attached to a pad of polymer material with adhesive. This conductive member is commercially sold by Lectec Corp. (Eaton, MN). FIGS. 2d and 2d' illustrate a conductive member 60 comprising a small square of metallic foil 62 which is attached to a cloth backing 64 with adhesive and contains a metallic lug 66 for attachment of a lead wire 68. The lug 66 penetrates through the backing 64 to make electrical contact with the metallic foil 62 square; this conductive member 60 form is sold by Empi, Inc. (Fridley, MN). Each of the conductive members illustrated in FIGS. 2a, 2b, 2c, 2d, and 2d' is suitable for use with the electrical circuitry and current source seen in FIG. 1.

In addition to these, however, it will be expressly understood that many other types of conductive members known in the art may be used with the assembly of FIG. 1. Regardless of their particular geometric configuration, chemical composition, physical dimensions, or electrical characteristics not all of these conductive members are useful with the present invention so long as electrical current is conveyed to the surface of the reservoir matrix.

When employing alternate source of energy, the specific means for conveying the energy from its source to the polymeric matrix will vary with the requirements of the particular energy source. For example, when laser energy is used, the conveying means comprises that portion of the air intermittent between the laser and the polymeric matrix as these are positioned and aligned one to the other. Similarly, with microwaves, the energy waves pass directly through the air or other environmental space as they travel towards the surface of the polymeric matrix. The air or other matter occupying the space thus comprise the conveyance means. In comparison, ultrasound energy requires a tangible interfacing medium such as water or conductive gel to be placed between the ultrasound energy source and the reservoir matrix for transmission of the energy waves. The interfacing medium thus comprises the conveying means. Lastly, the apparatus limitations of magnetism presently require the polymeric matrix to be placed as closely as possible to the origin of the oscillating magnetic field. As has been demonstrated by Siegel et al. [Pharmaceutical Research (1984)] an encased set of small magnetic beads is positioned on an exterior surface of the polymeric matrix; a triggering device positioned at a predetermined distance from these small beads acts to rotate and oscillate them thereby creating the magnetic field. Under these use circumstances, both the triggering device and the magnetic beads together comprise the means for conducting energy form its source to the polymeric matrix.

Characteristics Of And Compositions Comprising The Polymeric Matrix

In its broadest definition the material suitable for use as a polymeric matrix is a porous, hydrophilic, composition which supports a confluent aqueous phase and has an initial ohmic resistance not greater than 500 ohms per square inch in the absence of an electrically conductive salt solution above 1.0% in concentration. Each of these characteristics must be present within the matrix.

This polymeric matrix must be porous, having tiny holes or apertures through which a fluid may pass. Porosity—the total volumetric percentage of void space within the matrix—is not of consequence. The pore size—the individual dimensions or diameters of the cavities or apertures comprising the matrix—is also not a limitation except in the instance of transdermal delivery of pharmacologically active ligands. In such applications, the average diameter of the pore or cavity must be large enough for the neutral ligand molecule of interest and/or the ionized ligand species of interest to pass through the pore. In every other respect, the pore size need not conform to any set or minimal dimensions.

The polymeric matrix forming the reservoir must be physically and chemically stable under the intended use conditions. Regardless of the source or type of energy conveyed to the matrix, this material should not be subject to degradation and/or decomposition over a wide range of energy frequencies and powers. Similarly, materials which react with the pharmacologically active ligands to be delivered, physically or chemically, are also not suitable.

The polymeric matrix must be hydrophilic in nature—that is, the matrix material combines with water and aqueous preparations in general; whether the matrix material is also either wettable and/or water permeable to any degree is not of importance. In addition, the specific degree of hydrophilicity, as measured by any of the conventional methods, is irrelevant.

The polymeric matrix must also be able to support a confluent aqueous phase within the matrix proper. The term "confluent aqueous phase" is defined herein as the existence, albeit on a molecular scale, of water or a water based fluid which coats the individual pores in the matrix and flows through the pores as a collection of streams and channels of varying dimensions and volumes to form a continuous, discrete layer or phase within the polymer matrix which is not absorbed into and is not adsorbed onto the surface of the material comprising the matrix. "Absorption", as used herein, is defined as the taking up of a substance or fluid into the internal three-dimensional physical structure of a chemical composition comprising the matrix with a concomitant loss of physical identity for the substance or fluid so taken up. "Adsorption", as used herein, is defined as the fixation and adherence by physical or chemical action of a substance or fluid to the surface of a chemical composition comprising the matrix with a concomitant loss of mobility for the substance of fluid so fixed.

Lastly, the polymeric matrix must demonstrate an initial resistance not greater than 500 ohms per square inch. This 500 ohm per square inch limitation is a value to be determined in the absence of an electrically conductive salt solution above 1.0% in concentration and is exclusive of the resistance value(s) of any conductive member or other means for conveying energy from its source to the reservoir. As such, the initial resistance value is normally calculated mathematically by empirically determining the resistance values of the conveying means alone and in combination with the material comprising the polymeric matrix over the shortest measurable time period—recognizing that the longer the energy is applied, the greater the resistance values will become. It will be appreciated also that the units of resistance are ohms ($\Omega$) which are defined as joules/cm$^{-1}$ and thus are units not limited solely to electrical energy embodiments of the invention; rather, the ohm term is a meaningful and accurate unit of resistance in energy systems generally including laser light, ultrasound, microwave, and magnetism. The ohm unit is a true quantitative term for all these kinds of energy regardless of what specific form is actually employed with the electrode and electrode assembly.

The matrix material is preferably a polymeric composition which may be composed of a single monomer which has been cross-linked or be comprised of a co-polymer (formed by the union of at least two distinct compounds) which is itself then cross-linked by one or more specific agents to form a polymer. The geometric configuration of the polymeric matrix may be varied to meet the user's need or convenience, but it is preferable that the average thickness of the matrix be minimized—most preferably in the range of one to two millimeters, or failing that, be kept as thin as possible. Although two different chemical formulations are described herein as the preferred compositions for use as the polymeric matrix, the essential criterion which renders a composition, formulation, or material suitable for use within the present invention remains porosity, hydrophilicity, the ability to support a confluent aqueous phase, and demonstrable evidence of an initial ohmic resistance of (exclusive of conveyance means) not more than 500 ohms per square inch in the presence of one or more electrically conductive salt solutions whose concentration in total is not substantially more than 1.0% weight-to-volume. For this reason, many presently known compositions, formulations, and materials (natural and synthetic) now used for non-therapeutic applications, are expected to be suitable for use within the present invention. Many are polymers described in the literature both specifically and as general classes of compositions. Exemplifying such compilations are the texts of Yale L. Meltzer entitled *Water Soluble Polymers, Development Since* 1978, Noyes Data Corporation, 1981 and *Water-Soluble Polymers*, Noyes Data Corporation, 1972. As has been shown by these texts, the different classes of polymers believed useful as polymeric matrices in the present invention include the following: acrylamide polymers, acrylic acid and methacrylic acid polymers, alkyds, butadienes, carboxylic products, cellulose ethers and other cellulose products, epoxy products, ethylene oxide polymers and related products, fluoropolymers, formaldehyde products, gelatin and gelatin products, inorganic products, natural gums, polyamides and polyamids, polyesters, polyethylene, glycol derivatives, polyethylamine and related products, polysiloxanes and related products, polyurethane products, polyvinyl, alcohol and related products, polyvinyl pyrrolidone and related products, and similar polymeric compositions which do not easily fit into one of the aforementioned classes. As will be recognized, the two preferred specific embodiments of polymeric matrices useful in the present electrode apparatus as reservoirs are individually from different classes: to wit, a polyvinyl pyrrolidone polymer and a methacrylate polymer. Each of these will be described in detail.

Several other characteristics and properties are desirable within such compositions: the polymer should be non-toxic and biocompatible (non-irritating) with the subject's tissues; if a pharmacologically active ligand is to be delivered, the polymer should remain chemically neutral and/or non-reactive with the ligand of interest; the polymer should be stable over prolonged periods of time and withstand moderate cold and heat without degradation or decomposition; preferably, the polymer can be fabricated with ease and be configurable using conventional molding or casting techniques to meet predetermined dimensions and/or geometric configurations.

Figure 3A:
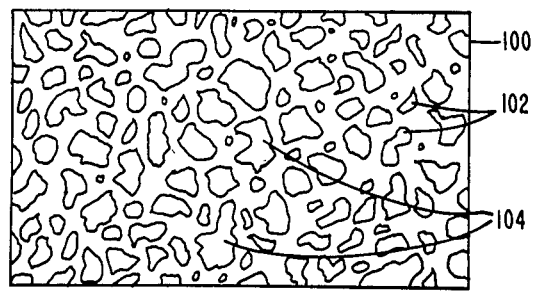
FIGS. 3a-3d represents cross-sectional views of the organizational configurations within different embodiments of the polymeric matrix in the present invention.
Figure 3B:
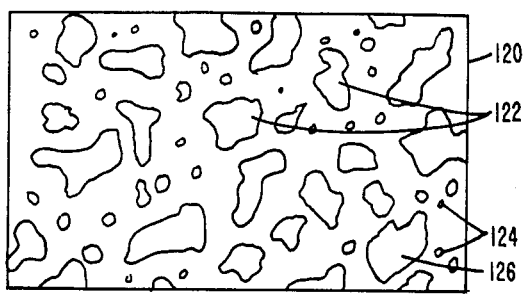

The internal structure or organization of the polymeric matrix will undoubtedly vary not only with the specific chemical monomers used, but also with the range of proportions for each ingredient, and the method of forming or casting the polymerized composition into three-dimensional configuration. For example, as is readily recognized and accepted in the art, the porosity, pore size, density, gelling characteristics and the like can be substantially altered by varying the ratios of specific reactants; by controlling the available quantities of air during casting; and by varying the reaction temperatures and/or pressures during the polymerization process. The effects obtained by varying these factors are shown by FIGS. 3a–3d which pictorially illustrate in cross-sectional views the variety of porous structural and organizational configurations which may be attained without regard to the specific chemical formulation comprising the polymeric material. FIG. 3a illustrates a polymeric matrix 100 in which the pores or cavities 102 are consistently uniform and regular thereby forming a series of long flowing conduits of relatively even diameter throughout the entirety of the matrix. The interstitial spaces 104, the void volume of the pores themselves, are similar in size and in structural organization throughout the polymer. In comparison, FIG. 3b shows an internal matrix structure 120 of large cavities or pores 122 which are in communication with a series of smaller diameter interconnecting channels 124; the interstitial spaces 126 of the matrix in FIG. 3b thus includes both the large pores or pockets and the adjoining interconnecting channels which form longer, more tortuous pathways within the matrix from one external surface to the other. It is readily seen that the pores are neither uniform, nor regular, nor have a common diameter or shape. In comparison with the matrix of FIG. 3a, the matrix of FIG. 3b is substantially equivalent in overall porosity (total void volume) but is distinctly different in both pore shape and size and in the quantitative number of pores irrespective of their diameter of configuration.

Figure 3C:
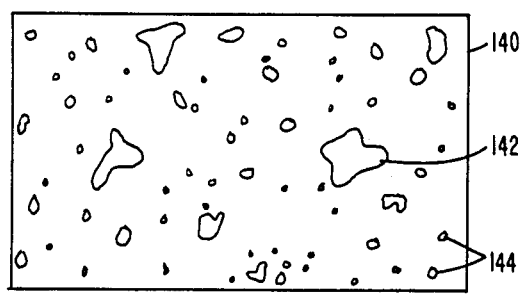
Figure 3D:
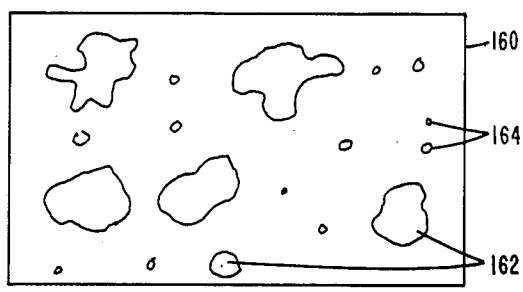

The polymeric matrix 140 illustrated in FIG. 3c is another variant of the structural organization illustrated in FIG. 3a but shows an even more tortuous series of interstitial spaces and a much greater disparity of diameters between the pores 142 and the interconnecting channels 144. The matrix 160 as seen in FIG. 3d is a more extreme example of that in FIG. 3b. The total porosity has been markedly reduced and the differences in size between the comparably large pores 162 and the greatly diminished interconnecting channels 164 have grown. Assuming, for illustrative purposes only, that the polymeric compositions forming the matrices of FIGS. 3b and 3d are identical, it is apparent that the matrix of FIG. 3d is comparably more dense, less porous, and has a greater variety of size for its pores and interconnecting channels to that in FIG. 3b. While the matrix organization of FIG. 3a may be most desirable, it is expressly understood that all the structural and organization matrices illustrated by FIGS. 3a-3d are useful in the present invention; moreover all other structural variations in format are also suitable for use as the polymeric matrix so long as the minimal critical criteria are met.

As regards the matrices illustrated in FIG. 3 as a whole, the total porosity of any matrix may vary from 5%-95% by volume regardless of chemical composition; the average mean diameter of the interstitial spaces (pores, cavities, or interconnecting channels of varying dimensions and configurations) is irrelevant so long as an aqueous confluent phase remains supportable. In some instances the pores should be sufficiently large to allow the pharmacologically active ligand of interest to physically pass therethrough either as a neutral molecule or as an ion species.

This last point deserves further elaboration. A critical feature of all polymeric matrices is that they by hydrophilic in nature and be capable of supporting a confluent, aqueous phase within its interstitial spaces. With reference to FIGS. 3a-3d, the aqueous medium lines the walls forming the pores and interconnecting channels as a continuous fluid phase. This aqueous phase may include specific additives such as salts, buffering compounds, and additives such as surface active agents. The aqueous phase resides within the interstitial spaces of the matrix as a discrete, confluent liquid layer that extends throughout the pores, cavities and interconnecting channels. It is not required, however, that this confluent aqueous phase partially or completely fill any of the interstitial spaces formed by the pores, cavities and/or interconnecting channels in the matrix to any degree; rather it is necessary only that the confluency of the aqueous medium be maintained and supported by the matrix material as an irregular but continuous fluid coating or phase which may vary in volume from zone to zone within the matrix proper.

The relationship between the polymeric composition forming the matrix and this aqueous phase is preferably one that holds the surface tension between them to a minimum. This is most desirable when ionized or neutral pharmacologically active ligands are introduced into the polymeric matrix. Such ligands become dispersed or solubilized within the aqueous phase and thus migrate through the matrix using the confluent aqueous phase as a vehicle. In this manner, the aqueous phase acts as a liquid carrier and serves to physically transport the ligand from one area of the matrix to another. When in communication with a conductive member (or other means for conveying energy to the matrix and sufficient energy), the ligand ions or neutral molecules are believed to be propelled out of the matrix into the tissues of the patient via this confluent aqueous phase carrier mechanism. Regardless of the energy source or the particular mechanism at work, it is believed that the presence of a confluent aqueous phase within the interstitial spaces of the polymeric matrix is necessary for ligand delivery to occur. As illustrated by each of the polymeric formulations, methods of matrix preparation, and examples which follow herein, the use of one or more electrically conductive salt solutions in concentrations substantially above physiological strength (1.0% weight/volume) is neither necessary nor desirable for electrical conductivity. Rather, the use of salts, pH adjustments, buffering compounds, and surface active agents (be they anionic, cationic or non-ionic) and the like in not substantially more than 1.0% concentrations (w/v) are believed to merely increase the degree of hydrophilicity between the polymer composition and the confluent aqueous phase—thereby reducing the surface tension of the aqueous medium itself and enhancing the speed and ease with which ligand migration through the matrix may be achieved.

It is desirable that the aqueous phase be present as a confluent fluid within the interstitial spaces in proportions ranging from 5%-95% of the matrix by volume and preferably comprise 25%-75% of the total volume. The inclusion of a surface active agent is an optional addition, the choice of which will vary with the characteristics of the individual matrix material, the porosity and pore size, and the composition's hydrophilicity. In many instances, no surfactant will be needed. However, in those instances where a surfactant is added, it is preferably used in concentrations of 0.1%-1.0% of the aqueous phase volume.

It is apparent that changing any one or more of the factors or parameters identified and described above will alter the physical and chemical characteristics of the polymeric matrix in some measurable degree. The sum of all the factors and parameters identified above is also directly affected by the initial ohmic resistance of the polymeric matrix (exclusive of the conductive member) as measured by Ohm's law. Regardless of the individual physical and chemical interrelationships, an initial ohmic resistance of not more than 500 ohms per square inch is required of all polymeric matrices intended for use with the present invention. The specific chemical compositions described hereinafter meet this ohmic resistance limitation, whereas materials from presently known electrodes for electrical nerve or muscle stimulation and/or transdermal drug delivery devices do not meet these criteria.

The preferred embodiments of polymeric compositions for use as the polymeric matrix in the present invention comprise a hydroxyethyl methacrylate polymer (hereinafter "HEMA") and a polyvinyl pyrrolidone polymer (hereinafter "PVP"). Each of these are described below.

HYDROXYETHYL METHACRYLATE (HEMA)

Hydroxyethyl methacrylate (HEMA) is a non-toxic biocompatible hydrogel formed by casting or molding a cross-linked polymer in an aqueous solution and allowing it to gel. This may be achieved by free radical polymerization of hydrophilic monomers such as hydroxyethyl methacrylate (HEMA) monomers or polymerization of copolymers comprising HEMA. It will of course be appreciated that many other hydrophilic methacrylate monomers and derivatives in addition to HEMA can be employed. The general procedures for such polymerization are described in Refojo, M.J., J. Appl. Poly. Sci., 9:3416-3426 (1965) and Holly et al., J. Biomed. Mat. Res., 9:315 (1975).

Hydrogel polymeric matrices comprising HEMA were prepared based upon the earlier published methods. Because the formed polymeric matrix is a hydrogel whose overall porosity, pore size, density, and total aqueous content may be modified for specific purposes, it will be recognized that the internal structure and organization of the HEMA polymer may take any of the physical forms illustrated in cross-section by FIGS. 3a-3d. A preferred HEMA matrix is made as follows: 1.0 milliliter (hereinafter "ml") of commercially obtained HEMA (Poly Sciences, Inc.) is combined with 1.0 ml of ethylene or propylene glycol, 1.0 ml of H$_2$O or buffer, 0.1 ml of 6% ammonium persulfate and 0.1 ml of 12% sodium metabisulfite added in sequence. After mixing these compounds together, the resulting clear viscous monomer solution was placed between two glass slides separated by two cover slips to maintain distance and allowed to polymerize by heating the mixture for two hours at 38° C. The approximate thickness of the formed polymeric matrix was 0.5 millimeters (hereinafter "mm"). This clear hydrogel was then dialyzed exhaustively against Tris-NaCl buffer (7.44) to remove residual monomer and residual ethylene glycol. During the dialysis step, the hydrogel may have become opaque in appearance, but returned to transparent form again after the exchange with water has been completed.

The range of proportions for HEMA, ethylene glycol, ammonium persulfate, and sodium metabisulfite may be varied from the preferred concentrations with the following results: Increases in the percentage volume of HEMA tends to increase both the viscosity of the formed polymer, and decrease the total porosity of the matrix. Increasing the proportion of ethylene or propylene glycol tends to decrease the time for polymerization with concomitant decreases in the quantity of aqueous fluid which can be retained by the polymer matrix.

When this hydrogel is used as a polymeric matrix for the transdermal delivery of pharmacologically active ligands (such as lidocaine, iodine, tetracycline and the like), the ligand may be added to the reaction mixture in the desired concentration prior to polymerization or be introduced into the hydrogel matrix after it has been formed using a liquid carrier such as an aqueous solution, colloid, or suspension, by dialysis, or by fluid exchange and other known methods. It is most preferable, however, that the ligand of interest be added directly to the aqueous admixture prior to polymerization in a quantity which will yield the desired concentration within the formed polymeric matrix. Two representative formulations using lidocaine hydrochloride (4% aqueous solution) are given in Table I below. Polymer A is to be found in Toselli et al., Journal of Ultrastructure Research 86:252-261 (1984); Additional details regarding Polymer B is to be found in Tracey et al., Cancer Chemotherapy and Pharmacology 10:96-99 (1983).

TABLE I

|  | POLYMER A | POLYMER B |
|---|---|---|
| HEMA monomer | 1.0 ml | 0.5 ml |
| ethylene or propylene glycol | 1.0 ml | 0.0 |
| 6% ammonium persulfate | 0.1 ml | 100 µl |
| 12% sodium metabisulfate | 0.1 ml | 0.0 |
| distilled H$_2$O [or buffer] | 0.5 ml | 0.25 ml |
| Lidocaine-HCl (4% solution) | 0.5 ml | 0.25 ml |
| divinyl benzene | 0.0 | 6 µl |
| TEMED [N, N, N', N'—] tetramethyl ethylene diamine | 0.0 | 10 µl |

Other hydrogels can also be prepared using methacrylate copolymers formed from several different methacrylate derivatives alone or in combination with hydroxyethyl methacrylate monomers. These other derivatives include, but are not limited to, methyl methacrylate, acrylic acid and acrylamide.

Cross-linking of the HEMA monomer using ethylene glycol or other known polyols or polyaldehydes is required to form the three-dimensional polymeric structure comprising the hydrogel. Sufficient cross-linkings may be obtained using a variety of other cross-linking agents including diacrylates, dimethacrylates, and similar divalent molecules. Under certain conditions, the HEMA monomer may be cross-linked using other techniques such as gamma irradiation or ultra violet irradiation. The polymerization process may be carried out in situ or using a bulk container or vessel of large size which will yield blocks, sheets or other configurations in large quantity which are subsequently mechanically reduced in size. In this instance, the sheets or blocks of hydrogel polymer are cut to the desired dimensions and then combined with the other components of the electrode in order to practice the invention.

POLYMERS OF N-VINYL PYRROLIDONE (PVP)

Polymers of N-vinyl Pyrrolidone (PVP) are non-toxic, biologically compatible gels useful as the matrix material in electrodes for nerve or muscular stimulation and/or for transdermal delivery of a pharmacologically active ligand. The preferred compositions comprising N-vinyl pyrrolidone (PVP) are those copolymers described in U.S. Pat. Nos. 3,44,907 and 3,563,968 in combination with a variety of cross-linking agents in any free-radical polymerization reaction now available in the art. The polymeric matrix preferably is a gel comprising a copolymer formed of a vinyl pyrrolidone monomer and an olefinic amine monomer such as allylamine as described in the cited prior art patents. The copolymer is subsequently polymerized using conventional methods with a cross-linking agent having at least two aldehyde groups available for chemical reaction. Such cross-linking agents are well known in the art and include anhydrides and dialdehyde derivatives of short chain, aliphatic dicarboxylic acids such as malonic acid, succinic acid, adipic acid and glutaric acid.

The preferred method of making the gel matrix follows the process of U.S. Pat. No. 3,494,907 and comprises making a copolymer of N-vinylpyrrolidone (hereinafter "VP") and allylamine (hereinafter "ALA") by free-radical polymerization. As used hereinafter, the term copolymer is coextensive with the definition in the prior art patents and includes all polymerizations of vinyl pyrrolidone monomer with any olefinic amine regardless of carbon chain length so long as it contains at least one unsaturated bond regardless of molar proportions. It is preferred that the unsaturated bond be in the alpha position as exemplified by allylamine. Reaction between the VP and the ALA is expected to occur at any molar ratio of VP:AlA ranging from 1:2 to greater than 1000:1, the preferred VP:AlA molar ratio ranging from 5:1 to 100:1 with a 25:1 ratio being optimal. The formed copolymer can have an average molecular weight ranging from 100 to 2 million daltons but preferably has a molecular weight in the range from 1,000 to 50,000 daltons, with an optimum molecular weight in the range from 5,000 to 25,000 daltons. It will be appreciated that the heaviest average molecular weight compositions for the copolymer are obtained when the VP:ALA molar ratio approaches infinity. However, with increasing molecular weight, the copolymer also becomes increasingly viscous and difficult to manipulate. For this reason, the 5,000-25,000 dalton compositions are most desirable.

When preparing the copolymer, the desired molar quantities of VP and ALA are combined in an organic solvent or mixture which is non-reactive with either monomer and does not enter into the reaction in any measurable degree. Such organic solvents are well known in the art and include various alcohols such as methanol, ethanol and the like which can be admixed with water as desired. Free-radical polymerization is begun using a catalyst or initiator of the free-radical type well known in the art such as peroxide catalysts including tertiaryalkyl organic peroxides and hydroperoxides; other initiators suitable for use are azocompound compositions such as azodiisobutylronitrile, and halogen photolythic moieties such as chlorine atoms. In the preferred mode, an organic peroxide catalyst ranging from 0.03 to 0.5 mole per mole of ALA is added and the reaction allowed to proceed with shaking at an elevated temperature from about 80° C. to aoout 200° C. for a time period ranging from 20 minutes to approximately 20 hours. The resultant copolymer is then isolated by precipitation into any organic ether such as diethylether with subsequent vacuum drying using conventional methods. When prepared in this manner, copolymer is produced in large quantities in which the VP:AlA ratio reflect the molar quantities of each mononer added to the reaction mixture. Although there may be some measurable quantity of N-vinylpyrrolidone homopolymer produced as a byproduct in the reaction, the major reaction product formed in substantial yield is the copolymer comprising VP and AlA.

It will be appreciated that alpha-olefinic amines other than allylamine are suitable for use as monomers when making the copolymer. These other aipha-olefinic amines are well known in the art and include 1-amino-3-butene, 1-amino-4-pentene, 2-amino-4-pentene, 1-amino-5-hexene and the like. In addition, olefinic primary amines having an unsaturated bond in other than the alpha position can be used if minimal steric hindrance to polymerization is shown. Each of these primary amines may be employed in place of allylamine in the above-described reaction.

The isolated copolymer is subsequently combined with water. The copolymer is very water-soluble and may be dissolved in water to make up concentrated solutions, the specific weight percent of the solution varying with the VP:AlA molar ratio and the average molecular weight of the copolymer.

It is preferred that a surface active agent such as sodium lauryl sulfate (hereinafter "SLS") be added to the copolymer solution prior to polymerization in a concentration representing 0.1-1.0 weight percent of the final preparation. Although anionic surfactants are preferred in most instances, non-ionic and cationic surface active agents may also be employed for specific preparations and uses. The aqueous admixture of copolymers and surface active agent is preferably adjusted to an optimum pH range of between 7.0-9.0 with concentrated sodium hydroxide prior to polymerization.

The preferred method of making the polymeric matrix gel combines concentrated copolymer solutions ranging from 20-40 weight percent of the final preparation with a cross-linking agent in concentrations from 0.05-1.00 weight percent and a surface active agent added in concentration of 0.1-1.0%. The preferred cross-linking agent is glutaraldehyde. Other cross-linking agents suitable for use are dialdehyde derivatives of short chain, aliphatic dicarboxylic acids such as malonic acid, succinic acid and adipic acid. The combining of cross-linking agent and aqueous copolymer/surfactant solution as a reaction mixture is best performed at room temperature followed preferably by casting of this fluid reaction mixture into a mold or other tangible form of specified geometry and predetermined dimensions for gelation. A gel matrix of firm consistency is formed within a time period controllable for up to 30 minutes, but is preferably formed within 3-10 minutes reaction time. The factors controlling speed of gelation are: the concentration of copolymer in the reaction mixture; the concentration of cross-linking agent in the reaction mixture; and the pH of the reaction mixture. Increasing the concentration of the copolymer and/or cross-linking agent shortens the time required for gelation. Similarly, increasing the pH of the mixture decreases gelation time. Conversely, lowering the concentrations of copolymer and/or cross-linking agent or lowering the pH of the reaction mixture increases gelation time.

It is preferred the pharmacologically active ligand be added directly to the polymerization reaction mixture in quantities which will yield 1%-5% in the final product. Alternatively, the ligand may be omitted from the polymerization reaction and be added instead to the cross-linked polymeric matrix at any time subsequent to its casting but prior to use. Under these conditions, the ligand is first combined with an aqueous liquid and this aqueous fluid is then combined with the formed polymeric matrix for transfer of the ligand by imbibation or solvent transfer.

Usually, however, it is far easier and more convenient to add the active ligand to the reaction mixture prior to the polymerization. A series of representative formulations employing lidocaine (as a 4% hydrochloride solution) are given in Table II below:

TABLE II

| COMPONENT | POLYMER A | POLYMER B | POLYMER C |
|---|---|---|---|
| copolymer | 1.21 g | 1.5 g | 1.5 g |

TABLE II-continued

| COMPONENT | POLYMER A | POLYMER B | POLYMER C |
|---|---|---|---|
| Lidocaine-HCl (4%) | 5.0 ml | 0.0 ml | 5.0 ml |
| water | 2.5 ml | 5.0 ml | 0.0 ml |
| pH (NaOH added) | 7.8 | 7.8 | 7.5 |
| glutaraldehyde | 0.1% | 0.6% | 0.8% |
| sodium lauryl sulfate | 0.1% | 0.1% | 0.1% |

Regardless of the exact chemical composition of the polymeric matrix, the materials are non-toxic, do not cause irritation when placed in contact with the human skin, and do not react with any ligand (drug, antibiotic, diagnostic or therapeutic agent) which is pharmacologically active. These polymeric matrices are particularly useful as a reservoir in the present invention for stimulation of nerves and muscles and for delivery of active ligands. They provide distinct advantages which include: the ability to incorporate therapeutic ligands into a preformer matrix having predetermined dimensions; improved adherence and conformability to the localized tissue site of the subject over substantial periods of time without disruption or detachment from the site surface; an indefinite shelf like; the ability to be used repeatedly without exhaustion; and the ability to receive electrical current repeated for nerve or muscle stimulation and/or for delivery of a ligand without degradation regardless of the specific geometric configuration or dimensions of the matrix.

II. SPECIFIC EMBODIMENTS, COMPARATIVE ANALYSES, AND APPLICATIONS OF THE INVENTION USING ELECTRICAL ENERGY

Tissue Stimulation

The electrode and electrode assembly useful for stimulation of internal tissues is that illustrated in FIG. 1. It employs AC, DC or both simultaneously and may take portable or bulk stationary form as is most convenient with respect to the application and the subject. The polymeric matrix comprises preferably either the HEMA or PVP polymer prepared as earlier described herein configured into the desired dimensions and shape. A generally useful matrix is a rectangular slab two inches long, two inches wide and 1-2 millimeters thick. The conductive members may be any of those shown in FIG. 2 or any other embodiment which has electrical communication with alternating and direct electrical current (household AC current, AC and DC generators, batteries, etc.). As stated previously, the voltages (AC and DC) may vary from 10-90 volts but preferably are in the range of volts with direct current; the current intensity is preferably maintained at a constant level (with concomitant changes in voltage in the range of from 0.1 ma to 10.0 ma (milliamperes) and is most useful when applied in the 3.5 ma-5.2 ma range; the time of application should be in the 5-60 minute range and is best kept to 15-30 minutes in duration.

Electrodes and electrode assemblies in accordance with the present invention utilize polymeric matrices which have a demonstrable initial ohmic resistance less than 500 ohms per square inch. As used herein, the term "resistance" will be used interchangeably with both AC and DC embodiments; this is technically incorrect in that electrical resistance properly refers to only direct current embodiments and is calculated simply by the formula $R = E/I$ where $E$ = energy measured in volts, $I$ = current intensity measured in amperes, and $R$ = resistance measured in ohms. In contrast, the AC embodiments use the term "impedance" for R which is calculated differently. Nevertheless the termms "resistance" and "impedance" are often used analogously or interchangeably in that ohms (joules/cm$^{-1}$) are the common unit. For simplicity and ease, therefore, only the term "resistance" will be used hereinafter. However, it will be understood that the resistance values for a single polymeric matrix material will vary greatly in accordance with whether alternating or direct current is used. Moreover, there are substantial differences between different polymeric compositions under similar or identical test conditions. For example, a selection of commercially manufactured electrodes for transcutaneous nerve stimulation which employ natural and synthetic polymers were compared to electrodes utilizing HEMA and PVP as the polymeric matrix. The HEMA and PVP matrices were prepared as the preferred embodiments without any active ligand as described previously. The conductive members used were those available from commercial sources, illustrated and described previously herein as FIG. 2a, 2c and 2d. The results are shown in Table III.

TABLE III

| ITEM (Source) | MATRIX | THICKNESS OF MATRIX (Approx.) | CONDUCTIVE MEMBER | COMBINED OHMIC RESISTANCE OF MATRIX AND CONDUCTIVE MEMBER AT: | |
|---|---|---|---|---|---|
| | | | | 20 HERTZ (AC) | 200 HERTZ (AC) |
| Staoderm "K" | Karaya gum | 1.38 mm | carbon sheet | 430 | 200 |
| Lectec (Lectec, Inc.) | Karaya gum | 3.06 mm | metallic foil sheet | 40.9 | 30.0 |
| Tenzcare (3M) | Synthetic Polymer | 1.53 mm | carbon sheet | 58.5 | 29.7 |
| SUE (Empi) | Karaya gum | 1.16 mm | metallic square | 25 | 12.6 |
| Neurostim (Conmed) | Synthetic Polymer | N/A | carbon sheet | 125 | 57 |
| Rodel | Karaya gum | 1.30 mm | metallic foil sheet | 74.7 | 46.5 |
| Sample 1 | HEMA | 1.50 mm | carbon sheet | 32.6 | 12.5 |
| Sample 1 | HEMA | 1.50 mm | metallic foil sheet | 16.8 | 14.5 |
| Sample 1 | HEMA | 1.50 mm | mettallic | 14.5 | 12.4 |

TABLE III-continued

| ITEM (Source) | MATRIX | THICKNESS OF MATRIX (Approx.) | CONDUCTIVE MEMBER | COMBINED OHMIC RESISTANCE OF MATRIX AND CONDUCTIVE MEMBER AT: | |
|---|---|---|---|---|---|
| | | | | 20 HERTZ (AC) | 200 HERTZ (AC) |
| Sample 2 | PVP | 1.3 mm | square carbon sheet | 39.4 | 25.0 |
| Sample 2 | PVP | 1.3 mm | metallic foil sheet | 25.4 | 15.0 |
| Sample 2 | PVP | 1.3 mm | metallic square | 19.9 | 14.8 |

Several conclusions are drawn from the data of Table I: first, although the ohmic resistance (AC) for each electrode is really the sum of the individual electrical resistances for the conductive member (carbon sheet, metallic foil sheet, or metallic foil square) *and* for the matrix material itself, it is apparent that the HEMA and PVP polymeric matrices demonstrate less electrical resistance than the other without regard to the nature of the conductive member in use. Second, the composition of the conductive member plays a major role in determining the empirically obtained ohmic values; by selecting different materials for use as the conductive member, the overall resistance may be increased or decreased. Therefore, recognizing that the greater the electrical resistance the more discomfort and irritation will likely occur to the subject and the less effective the electrode will be, it is far preferable that conductive members and matrices which in combination demonstrate the least electrical resistance be selected.

A preferred mode of using the electrode and electrode assembly earlier described and illustrated comprising either HEMA or PVP as the polymeric matrix is given by Examples A-C.

EXAMPLE A

The application is transcutaneous stimulation of peripheral motor nerves using alternating current (AC) in a subject with central motor pathway deficits resulting in spasticity. The subject is a human person afflicted with spasticity of the gastroc-soleus muscle group of the lower limb. Using the principle of reciprocal inhibition (Sherrington's Law), the deep peroneal nerve will be electrically stimulated resulting in inhibition of the gastroc-soleus muscle group and a reduction in spasticity. The stimulating (or transmitting) active electrode of FIG. 1 is placed over the anterior tibial nerve and tightly secured the indifferent (or oppositely positioned) active lectrode is placed just proximal to the patella. Stimulating alternating current is applied as a square waveform at 40 cycle per minute for 400 milliseconds over 30 minutes at a current intensity which is suprathreshold to the muscle, approximately 30-40 milliamperes. This can be repeated every four hours. A marked reduction in spasticity follows.

EXAMPLE B

The subject, the disorder, and the electrode assembly are identical to that described in Example A. In this application however, the gastroc-soleus muscle spasticity will be reduced directly by applying electrical current to the muscle itself. The transmitting active electrode is placed directly over the spastic muscle while the indifferent active electrode is positioned just proximal to the patella or over the tibialis anterior muscle. An alternating current in a square waveform is applied at a frequency of from 600–900 pulses per second at a current intensity of 20–40 milliamperes for 30 minutes. This is repeated every four hours or as needed. The current intensity is adjusted during stimulation to overcome the skin resistance and threshold of muscle contraction of the subject. Inhibition of spasticity occurs so long as the current is maintained. Spasticity of the tissue returns to its original level shortly following the end of treatment.

EXAMPLE C

The subject is a human person having a peripheral motor nerve deficit. The muscle tissue is to be stimulated directly using direct current applied via the electrode assembly of FIG. 1. The transmitting or stimulating active electrode is placed over the involved muscle. The indifferent active electrode is positioned at the same site parallel to the first at a distance of 3–4 centimeters. Direct current is applied to each electrode as a square waveform with a frequency of 1–10 hertz and a pulse duration in the range from 500–1000 microseconds with a current intensity of 20–40 milliamperes for 30 minutes. The working ranges allow for adjustments to be made with respect to the location, size and condition of the muscle being stimulated. The DC electrical stimulation retards atrophy of the musculature and prevents adhesion of the muscle to the surrounding connective tissues via repetitive contractions.

Iontophoretic Electrodes and Electrode Assemblies

A preferred embodiment of the present invention for transdermal delivery of pharmacologically active ligands is that earlier described in Part I and illustrated in FIG. 1. In iontophoretic applications however, direct (galvanic) current is utilized which polarizes each of the electrodes defined again as the conductive member (with or without connecting leads) and the polymeric matrix in combination as a unit in the assembly as either a positive or negative pole. The electrode containing the ligand to be delivered, known as the transmitting electrode, must receive a charge identical to that of the ligand in its ionized form; accordingly, if the ligand is positively charged in aqueous solution, the transmitting electrode apparatus must also become positively charged via the D.C. energy source. Alternatively, if the ligand ion species is negative in charge, the polarity of the transmitting electrode apparatus must also be negative. It is useful here to again state the essential criteria of polymeric matrices suitable for use in the present invention as reservoir materials which are exemplified by the HEMA and the PVP preparations. The matrices are hydrophilic, porous, able to support a confluent aqueous phase, and have an electrical resistance not greater than 500 ohms per square inch in the absence of an electrically conductive salt solution substantially above 1.0% in concentration (exclusive of the resistance for the conductive member). To demonstrate the effects of these parameters in combination with differing materials, a comparison of polymeric compositions used in commercially available tissue stimulating electrodes and the HEMA and PVP polymeric matrices was undertaken. The results are given in Tables IV–V. The conductive members used for measuring ohmic resistance are those commercially available embodiments previously described and illustrated herein in FIGS. 2a, 2c and 2d.

support a confluent aqueous phase within their respective compositions; it is believed that such aqueous fluid as may have existed in these gum preparations has been either absorbed or adsorbed within the polymer and can not exist as a discernable confluent liquid phase within the interstitial spaces of the composition itself. Second, the initial ohmic resistance of each electrode will vary with the choice of conductive member used to convey the current from its source to the polymeric matrix; the substantial variances among the different conductive members are believed to stem not only from their different chemical compositions, but also from differences in their thickness, their respective surface irregularities, and their ability (or inability) to adhere to the surface of

TABLE IV

| MATRIX MATERIAL (SOURCE) | HYDROPHILIC | DEGRADABLE BY D.C. CURRENT | CONFLUENT AQUEOUS PHASE | INITIAL RESISTANCE (OHMS) USING A CARBON SHEET CONDUCTIVE MEMBER AT 1.0 MILLIAMPERES |
|---|---|---|---|---|
| Karaya gum pad (STAODERM "K") | yes | not known | no aqueous phase | 2390 |
| Karaya Gum Polymer (Lectec, Corp.) | yes | not known | no aqueous phase | 3170 |
| Tenzcare Synthetic Polymer (3M Corp.) | yes | no | no aqueous phase | 2610 |
| SUE Karaya Gum Pad (Empi, Inc.) | yes | not known | no aqueous phase | 2300 |
| Neurostim Pad (Conmed Corp.) | yes | not known | no aqueous phase | 2250 |
| Synthetic Polymer Pad (Rodel Prod. Corp.) | yes | no | no aqueous phase | 2980 |
| dispersant device and membrance [Motion Control; U.S. Pat. No. 4,419,092] | no | no | no aqueous phase | 3870 |
| Urethane Pad (UNI-PATCH, Inc.) | no | no | no aqueous solution | 4780 |
| Aga-Agar [U.S. Pat. No. 4,383,529] | yes | yes | yes | 1280 |
| HEMA | yes | no | yes | 1250 |
| PVP | yes | no | yes | 1220 |

TABLE V

| | Initial Ohmic Resistance (Tested At 1.0 ma) | | | |
|---|---|---|---|---|
| CONDUCTIVE MEMBER (Source) | DIMENSION | KARAYA GUM (Empi) | KARAYA GUM (Lectec) | HEMA | PVP |
| Carbon Sheet (UNI-PATCH, Inc.) | 1⅜" × 1⅜" | 2300 | 2000 | 1250 | 1280 |
| Metallic Foil Sheet (Empi, Inc.) | 1 4/8" × 1 4/8" | 380 | 590 | 650 | 590 |
| Thin Metallic Square (Lectec, Corp.) | 1⅜" × 1⅜" | 700 | 370 | 590 | 790 |

Several conclusions may be made regarding the data of Tables IV and V. These are: first, that the various natural or synthetic karaya gum preparations regardless of source or presently known use, do not and can not the polymeric composition under test. Thirdly, each polymeric composition, regardless of its true chemical formulation, demonstrated an increased ohmic resistance due to polarization over time. However, the degree and speed of polarization, (electrical resistance) increased and varied greatly among the compositions; while the HEMA and PVP polymers showed small increases in ohmic resistance over several minutes, the karaya gum polymers exhibited massive increases in resistance, often in less than thirty seconds. Fourth, not all polymers are chemically stable under use conditions. The agar-agar gel degrades in the presence of direct current even at low voltages and amperages into small proteins, polypeptides and iodine ions; these breakdown products will migrate out of the gel and be delivered into the subject's tissues unintentionally. Similarly, karaya gum polymers melt at temperatures of 80° F. or greater and natural gums often contain undesirable contaminants which are irritating to the skin. Lastly, no one critical parameter of the polymeric matrix is dominant over the others. This is demonstrated by the data in Table IV which reveal that while some polymers have an initial ohmic resistance equal to or less than the value for HEMA and PVP, these compositions lack at least one of the remaining three critical requirements.

The interrelationship between the parameters of hydrophilicity, porosity, confluency of aqueous phase, and initial ohmic resistance thus is the critical key; this is best demonstrated by a single trait: the ability or inability of electrode assemblies to deliver pharmacologically active ligands transdermally using these polymers. Evidence of such ability or inability is illustrated by the examples which follow:

EXAMPLE 1

HEMA and PVP polymeric matrices containing 4% lidocaine hydrochloride were prepared as 1.5 mm×1⅝" squares as disclosed in Part I. Each lidocaine containing HEMA and PVP matrix was individually placed on an unobscure skin surface of a human subject, the precise location varying from an arm, leg, etc. A second HEMA and PVP matrix without any lidocaine was formed as a 1.5 mm×2"×4" pad and placed several inches opposite from the first. A carbon sheet conductive member sold by UNI-PATCH, Inc. of corresponding size was placed on the exposed surface of each HEMA and PVP matrix; each conductive member was joined by pin connector wires and alligator clips to a portable DC power supply (Motion Controls, Inc.). Direct current was applied to each electrode with the result that the lidocaine containing matrices became positively charged while the opposite matrices became negatively charged. The current intensity was steadily increased for HEMA matrices from 0-4 ma within 20 seconds and reached 5 ma within a total of 40 seconds. PVP matrices received current in increments of 1 ma per minute until 5.0 ma was applied. In both instances the 5.0 ma current was then maintained for 15 minutes. Testing for local anaesthesia at the delivery site was made using pressure sensitive monofilament sensory evaluation tools (Research Designs, Inc.). In each instance, local anaesthesia was induced at the delivery site.

EXAMPLE 2

HEMA and PVP polymeric matrices with and without 4% lidocaine hydrochloride were prepared and positioned within the electrode assembly as in Example 1. Direct current was applied to each electrode with increasing current intensity over the shortest possible time subject only to the subject's comfort and sensation. 5.0 ma intensity was usually reached in less than 40 seconds time and was then continued for 10 minutes. A preparation of karaya gum polymer containing 4% lidocaine (2 milligrams lidocaine per gram of karaya gum) was obtained from Lectec Corporation. Each of these polymers was then analyzed by high pressure liquid chromatography and spectrophotometry using known methods to verify that lidocaine was present within the karaya gum polymeric compositions prior to testing. When used with these electrode assemblies, all attempts to apply direct current at current intensities higher than 2.0-2.5 ma failed because of extreme discomfort to the subjects. For this reason, a maximum of 2.5 ma was applied and maintained over a 10 minutes period to the subject. The results of these attempts to iontophoretically induce anaesthesia are shown in Table VI.

TABLE VI

| POLYMERIC MATRIX MATERIAL | Transdermal Delivery of Lidocaine (4%) at: EFFECT |
| --- | --- |
| Karaya Gum Pad (Lectec, Corp.) | None |
| HEMA | Anaesthesia |
| PVP | Anaesthesia |

EXAMPLE 3

A 70 year old female patient suffers from uncontrollable muscle spasticity due to central nervous damage of unknown etiology. This is clinically verified and diagnostically identifiable using electromyography, a tracing technique which demonstrates the pattern of electrical nerve stimuli causing the uncontrollable muscle contractions. In this subject, many of the contractions are superficial muscle spasms of the face, throat and limbs. The recommended therapy is application of a local anaesthetic if it can be delivered locally and superficially into the skin without initiating systemic or general anaesthesia.

A HEMA polymeric matrix containing 4% lidocaine hydrochloride is prepared as described in Part I herein and formed as a 2"×4"×1.5 mm, rectangular pad. A second HEMA matrix without any lidocaine is formed as a 3"×5"×1.5 mm pad. The lidocaine containing matrix is placed on the neck of the patient laterally above the upper shoulder. The other HEMA matrix is positioned on the upper back over the upper trapezius muscle unilaterally. Carbon conductive members of appropriate size (UNI-PATCH, Inc.) are then disposed on the exposed exterior surface of each matrix; each conductive member is electrically connected via lead wires to a portable DC generator (Motion Controls, Inc.) as previously described. Iontophoretic delivery of lidocaine is performed sequentially by positioning the indifferent electrode on each side of the neck and applying direct current at 2.5 ma for fifteen minutes at each location.

Prior to iontophoretic delivery of lidocaine, EMG recordings of the muscle spasms in the patient were done in three modes: resting, maximum muscle contraction; and subsequent relaxation after contraction with the hands resting under the chin. A second set of EMG recordings was made immediately after the iontophoretic treatment in the identical three modes. A comparison of these EMG tracings for each respective mode both before and after treatment is illustrated in FIG. 4. As is readily apparent, the frequency and severity of the electrical nerve stimuli is greatly reduced by the delivery of lidocaine with a visible decrease of spasticity in the superficial muscles of the patient. Moreover, physical examination of the patient after lidocaine therapy showed a marked decrease in tremors, in uncontrollable muscle tone, and in pain.

EXAMPLE 4

The patient described in Example 3 was again treated by iontophoretic delivery of lidocaine 24 hours later using HEMA polymeric matrices for both the transmitting and receiving electrodes as earlier described. In this instance, however, neither HEMA matrix had *any* lidocaine incorporated into the reaction mixture prior to polymerization. Instead, a small quantity of commercially manufactured 2.5% xylocaine (lidocaine) ointment (Astra Pharmaceutical Products) was applied to the skin at the base of the neck before placing the HEMA matrix thereupon. The second HEMA matrix was again positioned unilaterally on the upper back over the trapezius muscle one side at a time. After placing the carbon conductive members on the exterior surface of each matrix, 2.5 ma of DC was applied to each electrode for 15 minutes. Comparisons of EMG tracings for this patient before and after iontophoretic treatment again demonstrated major differences similar to those illustrated in FIG. 4. Physical examination of the patient again revealed a marked decrease in tremors, in uncontrollable muscle tone, and in pain.

EXAMPLE 5

As a substitute for living tissues in analytical test procedures, a polyacrylamide gel block was prepared following the protocol of Lammeli, *Nature* 227:680 (1970). These polyacrylamide gels have a final concentration of acrylamide ranging from 5–10 percent. The basic procedure combines 30% acrylamide, 0.8% bisacrylamide, 1.5 M Tris-HCI (pH 8.7), distilled water, 10% ammonium persulfate, and 0.1 ml TEMED (N, N, N', N'-tetramethylethylenediamine) in liquid admixture. This mixture is degassed and allowed to polymerize by free radical polymerization to form a gel. This polyacrylamide liquid admixture is preferably poured into a small $3\frac{1}{2}''\times 2\frac{1}{4}''\times 3''$ glass mold for gelation into block form. Penetration of such polyacrylamide blocks by active ligands via iontophoretic electrode means is a recognized and valid analytical procedure.

The analytical technique requires the placement of the various polymeric compositions to be tested upon both exterior surfaces of the block, with the thickness of the block separating the electrodes under test. It is preferable to place the positively charged electrode at the bottom of the block and position the negatively charged matrix at the top. A series of experiments were performed to test HEMA matrices for ability to deliver methylene blue, bromophenol blue, and adriamycin. Methylene blue was prepared as a U.S. Pharmacopeia preparation and is an antiseptic and disinfectant. Bromophenol blue is a pH indicator and is prepared in indicator concentration (10%). Adriamycin is a brand name identification for doxorubicin hydrochloride, an anthracycline antibiotic, which is so cytotoxic that it is not to be given in dosages greater than 550 mg/m$^2$. Each of these therapeutic compounds was prepared as a dilute aqueous solution (4–5%) and combined with the *preformed* polymeric matrix for uptake of the ligand of interest to be delivered. Determinations were made by visual observation of chromaphoric migration into each block. The results are given in Tables VII and VIII.

TABLE VII

| POLYMER MATRIX | LIGAND | CURRENT INTENSITY DURATION | PENETRATION 7.5% POLY-ACRYLAMIDE/ BLOCK |
|---|---|---|---|
| HEMA | Adriamycin [orange] | 5.2 ma (¼ hr.) | ⅛″ |
| HEMA | Methylene Blue | 5.2 ma (1.2 hr.) | ¼″–½″ |
| HEMA | Bromophenol Blue | 5.0 ma (1.2 hr.) | ¼″ |

TABLE VIII

| MATRIX | LIGAND | CURRENT INTENSITY/ DURATION | PERCENT ACRYLAMIDE IN BLOCK | DEPTH OF PENETRATION |
|---|---|---|---|---|
| HEMA | Methylene Blue | 5.2 ma (1.2 hr.) | 5% | complete penetration (3.3 cm) |
| HEMA | Methylene Blue | 5.2 ma (1.2 hr.) | 7.5% | ¼″–½″ |
| HEMA | Methylene Blue | 5.2 ma (1.2 hr.) | 10.0% | ⅛″ |

EXAMPLE 6

Tetracycline radio-labeled with tritium [$^3$H] was purchased from New England Nuclear, Inc. as a prepared solution having 0.5–1.0Ci/mmol. The $^3$H-labeled tetracycline was added to the reactants given in Part I prior to polymerization. The formed $^3$H-tetracycline containing HEMA matrix was positioned at the bottom of a polyacrylamide block prepared as described in Example 5. A second HEMA matrix without any ligand was placed on the top of the polyacrylamide block in alignment with the first. Conductive members, electrical connectors, and the D.C. power source were attached to each HEMA matrix as previously described. With the application of DC power, the $^3$H-tetracycline containing matrix electrode became positively charged and began delivering $^3$H-tetracycline into the polyacrylamide block which was approximately 3.3 cm thick. The current intensity was maintained at 5.0 ma for 20, 40 or 60 minute durations respectively for a series of different blocks. At the end of each time period, several polyacrylamide blocks were analyzed by liquid scintillation for the quantity of $^3$H-tetracycline remaining at different depths within the blocks, the various concentrations of $^3$H-tetracycline being measured in cpm. The results showed that, on the average, 66% of the original $^3$H-tetracycline concentration in the HEMA matrix passed through the *entirety* of the block (3.3 cm) within 20 minutes; 77% of the original $^3$H-tetracycline concentration passed through the block within 40 minutes; and 92% passed through the block within 60 minutes.

Several conclusions may be drawn from the data presented by Examples 1-6 inclusive. First, polymeric compositions which meet the requisite criterion are useful as matrices within the electrode and electrode assembly described in FIG. 1 for iontophoretic transdermal delivery of pharmacologically active ligands; polymeric compositions which do not comply with the minimal requirements are inoperative under similar test conditions. Second, the preferred embodiments of the polymeric matrices, the HEMA and PVP compositions, are demonstrably able to deliver a broad range of ligands including anaesthetics (lidocaine), disinfectants (methylene blue), diagnostic dyes (bromophenol blue), and antibiotics (adriamycin and tetracycline). Third, the present invention provides the ability to control the degree of penetration of the ligand into the body; by raising the current intensity and/or duration of treatment, the ligand can be delivered in concentrated doses either superficially or deeply into the tissues.

The polymeric matrices embodied by the HEMA and PVP compositions when used in the electrodes and electrode assemblies described herein provide a noninvasive drug delivery system which may be also utilized for both transcutaneous electrical nerve stimulation and muscular stimulation. The polymeric matrices are: conformable to any surface regardless of irregularities; are not limited to a specific size or maximum surface area coverage; can be prepared with both minute or substantial volumes of liquid; can be used repeatedly without degradation; can be combined with the ligand in a variety of ways in advance of use; and can be positioned on any tissue surface at any location. This drug delivery system eliminates the systemic toxicity caused by parenteral injection and reduces the likelihood of accidental infection and complications caused by syringes and other invasive systems.

III. OPERATING MODALITIES

The present invention comprises an electrode apparatus and electrode assembly that may be used in a number of different modes for therapeutic purposes. For illustrative purposes only, an electrical energy embodiment of the invention will be presumed so as to more easily describe the various possible modes. The complete electrode assembly preferably has an electrical energy source which comprises all necessary switches and circuitry to select for waveform, alternating current and direct current and multiple settings for energy flow, each to begin and end at preselected times cyclically. The circuitry of the energy source therefore permits various combinations of no current, alternating current and direct current to be used alternatively and/or simultaneously in series within a 24-hour day, this series to be repeatable indefinitely for a desired number of days in succession.

Presuming the transmitting electrode to contain a pharmacologically active ligand the electrode and the electrode assembly as a whole may be employed in at least 4 different therapeutic modes which may be combined in whole or part.

Mode 1: Passive and Active Transdermal Ligand Delivery

The polymeric matrix containing the active ligand when placed on the skin surface will act as a passive carrier for slow release of the ligand across the tissues, as in presently known passive drug delivery systems. The active ligand may be any of the many anaesthetics, antibiotics, low molecular weight compositions (nitroglycerin and scopolamine), polypeptides, and macromolecules such as enzymes, vitamins, antibodies and hormones. So long as no energy is conveyed from the source to the polymeric matrix, the active ligand will be released only passively using a mechanism based on diffusion, solubility, or concentration density gradients, skin pH, temperature, salt content, or any combination of these. Such a mode of use allows for slow, uncontrolled release of ligand which is useful in many instances, but allows an immediate application of direct current when concentrated quantities of the drug are required as in emergency situations. An obvious clinical application is the addition of nitroglycerin to the polymer matrix which is used as usual in a passive mode so that a continuous but dilute concentration of the drug reaches the heart. However, should an emergency occur, the user may apply direct current to the matrix overlaying the upper thorax and thereby drive therapeutic quantities of the nitroglycerin to the heart muscle via the venous circulation; the ability to deliver such concentrated doses depends upon the subject initiating the delivery himself but is always available on demand should the need arise.

Mode 2: Repetitive Ligand Delivery and Multiple Ligand Delivery

This mode contemplates the need for a concentrated dosage of an active ligand to be delivered at specified times on a regular time schedule repeatedly. The timer circuitry within the energy source is set such that a specific amperage of direct current is conveyed to the polymeric matrix containing the ligand only at a selected time. The timer circuits allow the user to preset a schedule per hour or per day in accordance with the physician's medication regimen, as for example every 4 hours, every 12 hours, or any other time period. Once set at the preferred timing cycle, the specific waveform, and current intensity (DC) will be conveyed to the polymeric matrix at the desired times and the ligand delivered into the specified target zone without further attention. In this instance, the matrix contains a sufficiently large quantity of the ligand so that multiple doses may be delivered in succession. It is anticipated that the user will periodically introduce additional quantities of the ligand into the matrix or preferentially remove the original polymeric matrix and replace it with another. Moreover, as additional medication is prescribed, the original may be replaced with matrices containing different drugs. Alternatively, the user can combine several kinds of ligands within a single polymeric matrix to be delivered simultaneously or align several transmitting electrodes within one assembly, each electrode being set to deliver a single different ligand at a specific time. The sole restriction for multiple ligand delivery is that each ligand be compatible chemically with the polymeric matrix.

Mode 3: Alternating Current and Direct Current Used Simultaneously

The electrical energy source preferably is designed to allow alternating current and direct current to be applied to each electrode simultaneously as well as in the alternative. AC power in various waveforms and frequencies is applied to the matrices in order to stimulate nerves, to lower skin resistance to ligand delivery, and to provide an afferent block of sensory units. DC power, preferably as a continuous wave, is also applied to the matrix of each electrode simultaneously and actively drives the ligand in the matrix of the transmitting electrode. Within this mode, the AC can also be given as a series of pulses per second while the DC is given as a uniform current intensity over a different time period.

Mode 4: In Vivo Implants

The HEMA and PVP polymeric compositions, being non-toxic and biocompatible, provide matrices which may be surgically implanted in vivo within tissues. The electrode, comprising the conductive member and the polymeric matrix (containing a pharmacologically active ligand), may be implanted subcutaneously in tissues with major benefits. For example, any surgical procedure with a likelihood of post operative scarring can be effectively controlled by implanting a polymeric matrix containing beta-aminoproprionitrile fumarate into the tissue immediately before closing the surgical field; the electrical leads from the conductive member will extend from beneath the skin to an external source of electrical energy. Application of direct current will deliver sufficient quantities of the drug locally to prevent scarring; during interim periods, the matrix will act passively to continuously deliver small amounts of the drug as well.

It will be appreciated that the modes described above comprise active ligand delivery systems in combination with passive delivery systems, and with means for electrical stimulation of nerves and muscles. The effects of using active ligand delivery systems with these other AC and DC therapies provide benefits unavailable and unknown heretofore. Each individually and in combination is within the scope of the present invention as a whole. Recognizing that many operational parameters may be now selected to meet the user's need or convenience, the invention is not to be restricted in form or limited in scope except by the claims appended hereto.

What we claim is:

1. An electrode to be used with a source of energy for active transdermal delivery of a pharmacologically active ligand to a subject comprising:
   a hydrophilic, porous, polymeric matrix which supports a confluent aqueous phase and has an initial ohmic resistance not greater than 500 ohms per square inch in the absence of an electrically conductive salt solution substantially above 1.0% in concentration;
   a pharmacologically active ligand in communication with said polymeric matrix; and
   means for conveying energy from the energy source to said polymeric matrix.

2. A complete electrode for active transdermal delivery of a pharmacologically active ligand to a subject comprising;
   a source of energy;
   a hydrophilic, porous, polymeric matrix which supports a confluent and has an initial ohmic resistance not greater than 500 ohms per square inch in the absence of an electrically conductive salt solution substantially above 1.0% in concentration;
   a pharmacologically active ligand in communication with said polymeric matrix; and
   means for conveying said energy from said source to said polymeric matrix.

3. An electrode assembly for active transdermal delivery of a pharmacologically active ligand to a subject comprising:
   a source of energy;
   a plurality of electrodes, at least one of said electrodes comprising a hydrophilic, porous, polymeric matrix which supports a confluent aqueous phase and has an initial ohmic resistance not greater than 500 ohms per square inch in the absence of an electrically conductive salt solution substantially above 1.0% in concentration;
   a pharmacologically active agent in communication with said polymer matrix; and
   means for conveying said energy from said source to each of said electrodes.

4. The electrode as recited in claim 1, 2, or 3 wherein said energy is selected from the group consisting of galvanic electrical energy, laser light energy, ultrasound energy, microwave energy and magnetic energy.

5. The electrode as recited in claim 1, 2, or 3 wherein said polymeric matrix is selected from the group consisting of acrylamide polymers, acrylic acid polymers, methacrylic acid polymers, alkyds, butadienes, carboxylic polymers, cellulose containing products, epoxy products, ethylene oxide polymers and derivatives, fluoropolymers, formaldehyde products, gelatin and gelatin derivatives, inorganic products, natural gums, polyamides, polyimides, polyesters, polyethylene glycol polymers, polyethylamine and derivative products, polysiloxane and derivative products, polyurethane products, polyvinyl alcohol and related products, polyvinyl pyrrolidone and related products, starch and starch derivatives.

6. The electrode as recited in claim 1, 2, or 3 wherein said polymeric matrix comprises N-vinyl pyrrolidone.

7. The electrode as recited in claim 1, 2, or 3 wherein said polymeric matrix comprises hydroxyethyl methacrylate.

8. The electrode as recited in claim 1, 2, or 3 wherein said pharmacologically active agent is one selected from the group consisting of antibiotics, anaesthetics, steroids, vitamins, and hormones.

9. The electrode as recited in claim 1, 2, or 3 wherein said pharmacologically active ligand is dispersed within said matrix.

10. The electrode as recited in claim 1, 2, or 3 wherein said pharmacologically active ligand is disposed adjacent to said matrix.

11. The electrode as recited in claim 1, 2, or 3 wherein said confluent aqueous phase of said polymeric matrix includes at least one selected from the group consisting of inorganic salts, buffers, and surface active agents.

12. A method for making an electrode to be used with a source of energy for active transdermal delivery of a pharmacologically active ligand to a subject comprising the steps of:
    preparing a hydrophilic, porous, polymeric matrix which supports a confluent aqueous phase and has an initial ohmic resistance not greater than 500 ohms per square inch in the absence of an electrically conductive salt solution substantially above 1.0% in concentration;
    combining said polymeric matrix with means for conveying energy from the energy source to said matrix; and
    placing a pharmacologically active ligand in communication with said matrix.

13. A method for making a complete electrode for active transdermal delivery of a pharmacologically active ligand to a subject comprising the steps of:
- preparing hydrophilic, porous polymeric matrix which supports a confluent aqueous phase and has an initial ohmic resistance not greater than 500 ohms per square inch in the absence of an electrically conductive salt solution substantially above 1.0% in concentration;
- placing a pharmacologically active ligand in communication with said polymeric matrix; and
- joining said polymeric matrix to a source of energy whereby energy from said source is conveyed to said matrix.

14. A method for active transdermal delivery of a pharmacologically active ligand to a subject comprising the steps of:
- preparing a plurality of electrodes, each comprising a source of energy, a polymeric matrix, and means for conveying energy from said source to said polymeric matrix, at least one of said matrices being hydrophilic and porous, supporting a confluent aqueous phase, and having an initial ohmic resistance not greater than 500 ohms per square inch in the absence of an electrically conductive salt solution substantially above 1.0% in concentration;
- placing a pharmacologically active ligand in communication with one of said polymeric matrices;
- placing said electrodes onto the tissue of the subject; and
- conveying energy from said source to each of said electrodes.

15. The method as recited in claim 12, 13, or 14 wherein said preparation step includes a polymeric matrix comprising hydroxyethyl methacrylate.

16. The method as recited in claim 12, 13, or 14 wherein said preparation step includes a polymeric matrix comprising N-vinyl pyrrolidone.

17. The method as recited in claim 12, 13, or 14 wherein said confluent aqueous phase of said polymeric matrix includes at least one selected from the group consisting of inorganic salts, buffers, and surface active agents.

18. The method as recited in claim 13 or 14 wherein said preparation step includes an energy source selected from the group consisting of galvanic electrical energy sources, laser light energy sources, ultrasound energy sources, microwave energy sources and magnetic energy sources.

19. The method as recited in claim 14 further comprising introducing sinusoidal electrical energy to at least one of said electrodes.

20. The method as recited in claim 19 wherein galvanic electrical energy is used in combination with said sinusoidal electrical energy.

21. A system for active transdermal delivery of a pharmacologically active ligand to a subject comprising:
- a pharmacologically active ligand in communication with a polymeric matrix, said matrix comprising a hydrophilic, porous polymer supporting a confluent aqueous phase and having an initial ohmic resistance not greater than 500 ohms per square inch in the absence of an electrically conductive salt solution substantially above 1.0% in concentration;
- an electrode assembly comprising a plurality of active electrodes in which at least one of said electrodes comprises said polymeric matrix and pharmacologically active ligand in combination, a source of energy, and means for conveying said energy from said source to said polymeric matrix;
- means for positioning said electrode assembly on the tissue of the subject; and
- means for controlling the conveyance of energy from said source to said polymeric matrix.

22. A system for active transdermal delivery of a pharmacologically active ligand to a subject comprising: the steps of:
- a pharmacologically active ligand in contact with a polymeric matrix, said matrix comprising a hydrophilic, porous polymer supporting a confluent aqueous phase and having an initial ohmic resistance not greater than 500 ohms per square inch in the absence of an electrically conductive salt solution substantially above 1.0% in concentration;
- an electrode assembly comprising a plurality of electrodes in which at least one of said electrodes comprises said polymeric matrix and said pharmacologically active ligand in combination, a source of galvanic electrical energy, and means for conveying said galvanic electrical energy from said source to said matrix;
- means for positioning said electrode assembly on the tissue of the subject; and
- means for controlling the conveyance of said galvanic electrical energy from said source to said polymeric matrix.

23. The transdermal delivery system as recited in claim 21 wherein said energy source is one selected from the group consisting of laser light energy sources, ultrasound energy sources, microwave energy sources, and magnetic energy sources.

24. The transdermal delivery system as recited in claims 21 or 22 wherein a plurality of pharmacologically active ligands are in communication with said polymeric matrix.

25. The transdermal delivery system as recited in claim 21 or 22 wherein said pharmacologically active ligand is dispersed within said polymeric matrix.

26. The transdermal delivery system as recited in claim 21 or 22 wherein said pharmacologically active ligand is disposed on the surface of the subject's tissue and is adjacent to said polymeric matrix.

27. The transdermal delivery system as recited in claim 21 or 22 wherein said pharmacologically active ligand is one selected from the group consisting of antibiotics, anaesthetics, steroids, vitamins, and hormones.

* * * * *